US007125841B2

(12) United States Patent
Sheehan

(10) Patent No.: US 7,125,841 B2
(45) Date of Patent: Oct. 24, 2006

(54) MUTANT HUMAN FACTOR IX WITH AN INCREASED RESISTANCE TO INHIBITION BY HEPARIN

(75) Inventor: John P. Sheehan, Middleton, WI (US)

(73) Assignee: The University of Texas Systems, San Antonio, TX (US)

( * ) Notice: Subject to any disclaimer, the term of this patent is extended or adjusted under 35 U.S.C. 154(b) by 171 days.

(21) Appl. No.: 10/416,952

(22) PCT Filed: Nov. 13, 2001

(86) PCT No.: PCT/US01/47276

§ 371 (c)(1), (2), (4) Date: Nov. 24, 2003

(87) PCT Pub. No.: WO02/40544

PCT Pub. Date: May 23, 2002

(65) Prior Publication Data

US 2004/0110675 A1 Jun. 10, 2004

Related U.S. Application Data

(60) Provisional application No. 60/248,326, filed on Nov. 14, 2000.

(51) Int. Cl.
*A61K 35/14* (2006.01)
*A61K 38/00* (2006.01)

(52) U.S. Cl. .......................... 514/2; 514/802; 530/380; 530/384

(58) Field of Classification Search ..................... None
See application file for complete search history.

(56) References Cited

U.S. PATENT DOCUMENTS

| | | | |
|---|---|---|---|
| 4,994,371 | A | 2/1991 | Davie et al. |
| 5,171,569 | A | 12/1992 | Anson et al. |
| 5,521,070 | A | 5/1996 | Meulien |
| 5,614,500 | A | 3/1997 | Zimmermann |
| 5,639,857 | A | 6/1997 | Zimmermann |
| 5,681,746 | A | 10/1997 | Bodner et al. |
| 5,814,716 | A | 9/1998 | Jallat et al. |
| 5,935,935 | A | 8/1999 | Connelly et al. |
| 6,034,222 | A | 3/2000 | Fischer et al. |
| 6,063,909 | A | 5/2000 | Huang et al. |
| 6,093,392 | A | 7/2000 | High et al. |

FOREIGN PATENT DOCUMENTS

| | | |
|---|---|---|
| EP | 0195592 | 9/1986 |
| EP | 0430930 | 6/1991 |
| WO | WO 84/00560 | 2/1984 |
| WO | WO 98/33907 | 8/1998 |
| WO | WO 99/03496 | 1/1999 |
| WO | WO 02/40544 | 5/2002 |

OTHER PUBLICATIONS

Chang et al. Changing Residue 338 in Human Factor IX from Arginine to Alanine Causes an Increase in Catalytic Activity. (May 15, 1998) J. Biol. Chem. vol. 273, No. 20, pp. 12089-12094.*
Nishimura et al. Characterization of Factor IX Fukuoka with Substitution of Asn-92 by His in the 2nd Epidermal Growth Factor-Like Domain. (1991) Thromb. Haemost. vol. 65, No. 6, p. 712.*
Andersson, "Purification and characterization of human factor IX," Thrombosis Research 7:451-459, 1975.
Austen et al., "A laboratory manual of blood coagulation," Blackwell Scientific Publishing, 1975.
Bajaj et al., "Human factor IX and factor IXa," Meth. Enzymol. 222:96-128, 1993.
Banner et al., "The crystal structure of the complex of blood coagulation factor VIIa with soluble tissue factor," Nature 380:41-46, 1996.
Barrow et al., "Inhibition by heparin of the human blood coagulation intrinsic pathway factor X activator," J. Biol. Chem. 269:26796-26800, 1994.
Bessos et al., "Immunopurification of human coagulation factor IX using monoclonal antibodies," Thromb. Haemostas. 56:86-89, 1986.
Better et al., "*Escherichia coli* secretion of an active chimeric antibody fragment," Science 240:1041-1043. 1988.
Bitter et al., "Secretion of foreign proteins from *Saccharomyces cerevisiae* directed by α-factor gene fusions," Proc. Natl. Acad. Sci. USA 81:5330-5334, 1984.
Brandstetter et al., "X-ray structure of clotting factor IXa: Active site and module structure related to Xase Activity and hemophilia B," Proc. Natl. Acad. Sci. USA 92:9796-9800, 1995.
Busby et al., "Expression of active human factor IX in transfected cells," Nature 316:271-273, 1985.
Chang et al., "Changing residue 338 in human factor IX from arginine to alanine causes an increase in catalytic activity," J. Biol. Chem. 273:12089-12094, 1998.
Cote et al., "Characterization of a stable form of human meizothrombin derived from recombinant prothrombin (R155A, R271A, and R284A)," J. Biol. Chem. 269:11374-11380, 1994.
Engelhard et al., "The insect tracheal system: A conduit for the systemic spread of *Autographa californica* M nuclear polyhedrosis virus," Proc. Natl. Acad. Sci. USA 91:3224-3227, 1994.
Evans et al., "Molecular cloning of a cDNA encoding canine factor IX," Blood 74:207-212, 1989.
Fay et al., "Molecular for the factor VIIIa-dependent decay of the intrinsic factor Xase," J. Biol. Chem. 271:6027-6032, 1996.
Galeffi et al., The propeptide region of clotting factor IX is a signal for a vitamin K dependent carboxylase: evidence from protein engineering of amino acid -4, Nucl. Acids. Res. 15:9505-9513, 1987.
Hamaguchi et al., Expression and characterization of human factor IX, *J. Biol. Chem.* 266:15213-15220, 1991.

(Continued)

*Primary Examiner*—Nashaat T. Nashed
*Assistant Examiner*—Holly Schnizer
(74) *Attorney, Agent, or Firm*—Marshall, Gerstein & Borun LLP

(57) ABSTRACT

The present invention is related to a novel composition of matter and methods of using the same. More particularly, the invention describes mutant human factor IX which has an increased resistance to inhibition by heparin. Methods of making and using this composition for the therapeutic intervention of hemophilia are disclosed.

11 Claims, 6 Drawing Sheets

OTHER PUBLICATIONS

Hathaway et al., "Laboratory measurement of hemostasis and thrombosis," In: Disorders of Hemostastis and Thrombosis: A Clinical Guide, pp. 21-29, 1993.

Hirsh et al., "Heparin: Mechanism of action, pharmacokinetics, dosing considerations, monitoring, efficacy, and safety," Chest 108(4 Suppl): 258S-275S, 1995.

Hoffman et al., "Factors IXa and Xa play distinct roles in tissue factor-dependent initiation of coagulation," Blood 86:1794-1801, 1995.

Holmer et al., "The molecular-weight dependence of the rate-enhancing effect of heparin on the inhibition of thrombin, Factor Xa, Factor IXa, Factor Xlla and kallikrein by antithrombin," Biochem. J. 193:395-400, 1981.

Hopfner et al., "Coagulation factor IXa: the relaxed conformation of Tyr99 blocks substrate binding," Structure 7:989-996, 1999.

Huang et al., "Molecular defect in factor $IX_{Hilo}$, a hemophilia $B_m$ variant: Arg—Gln at the carboxyterminal cleavage site of the activation peptide," Blood 73:718-721, 1989.

Jordan et al., "The kinetics of hemostatic enzyme-antithrombin interactions in the presence of low molecular weight heparin," J. Biol. Chem. 255:10081-10090, 1980.

Kaufman et al., "Expression, purification, and characterization of recombinant γ-carboxylated factor IX synthesized in Chinese hamster ovary cells," J. Biol. Chem. 261:9622-9628, 1986.

Kung et al., "Human factor IX corrects the bleeding diathesis of mice with hemophilia B," Blood 91:784-790, 1998.

Kurjan et al., "Structure of a yeast pheromone gene (*MF*α): A putative α-factor precursor contains four tandem copies of mature α-factor," Cell 30:933-943, 1982.

Larson et al., "Structural integrity of the γ-carboxyglutamic acid domain of human blood coagulation factor IXa is required for its binding to cofactor Vllla," J. Biol. Chem. 271:3869-3876, 1996.

Lawson et al., "A model for the tissue factor pathway to thrombin," J. Biol. Chem. 269:23357-23366, 1994.

Liebman et al., "Immunoaffinity purification of human factor IX using conformation-specific polyclonal and monoclonal antibodies," Blood 62, suppl. 1, 288a, Abstract π 1055, 1983.

Liebman et al., "Immunoaffinity purification of factor IX (Christmas factor) by using conformation-specific antibodies directed against the factor IX-metal complex," Proc. Natl. Acad. Sci. USA 82:3879-3883, 1985.

Lin et al., "A coagulation factor IX-deficient mouse model for human hemophilia B," Blood 90:3962-3966, 1997.

Mathur et al., "Interaction of factor IXa with factor Vllla," J. Biol. Chem. 272:23418-23426, 1997.

Mauray et al., "Mechanism of factor IXa inhibition of antithrombin in the presence of unfractionated and low molecular weight heparins and fucoidan," Biochim. Biophys. Acta. 1387:184-194, 1998.

McNeely et al., The anticoagulant mechanism of action of heparin in contact-activated plasma: inhibition of factor X activation, Blood 65:1226-1231, 1985.

Meulien et al., "Increased biological activity of a recombinant factor IX variant carrying alanine at position+1," Prot. Engineer. 3:629-633, 1990.

Neels et al., "Activation of factor IX zymogen results in exposure of a binding site for low-density lipoprotein receptor-related protein," Blood 96:3459-3465, 2000.

Noyes et al., "Identfication of the molecular defect in factor $IX_{Chapel\ Hill}$: Substitution of histidine for arginine at position 145," Proc. Natl. Acad. Sci. USA 80:4200-4202, 1983.

Olson et al., "Quantitative characterization of the thrombin-heparin interaction" J. Biol. Chem., 266:6342-6352, 1991.

Pieters et al., "Inhibition of factor $IX_a$ and $X_a$ by antithrombin lll/heparin during factor X activation," J. Biol. Chem. 263:15313-15318, 1988.

Pieters et al., "Heparin-stimulated inhibition of factor IXa generation and factor IXa neutralization in plasma," Blood 76:549-554, 1990.

Price et al., "Expression, purification and characterization of recombinant murine granulocyte-macrophage colony-stimulating factor and bovine interleukin-2 from yeast," Gene 55:287-293, 1987.

Rand et al., "Blood clotting in minimally altered whole blood," Blood 88:3432-3445, 1996.

Rees et al., "The role of β-hydroxyaspartate and adjacent carboxylate residues in the first EGF domain of human factor IX," EMBO J. 7:2053-2061, 1988.

Rose et al., "Propagation and expression of cloned genes in yeast: 2-μm circle-based vectors," Meth. Enzymol. 185:234-279, 1990.

Sheehan et al., "Molecular mapping of the heparin-binding exosite of thrombin," Proc. Natl. Acad. Sci. USA 91:5518-5522, 1994.

Sheehan et al., "Phosphorothioate oligonucleotides inhibit the intrinsic tenase complex," Blood 92:1617-1625, 1998.

Sheehan et al., "Heparin allosterically modulates intrinsic tenase activity through a regulatory exosite on factor IXa," Blood 96:633a, abstract #2720, 2000.

Smith et al., "Molecular engineering of the *Autographa californica* nuclear polyhedrosis virus genome: Deletion mutations within the polyhdrin gene," J. Virol. 46:584-593, 1983.

Snyder et al., "Correction of hemophilia B in canine and murine models using recombinant adeno-associated viral vectors," Nature Med. 5:64-70, 1990.

Stearns et al., "Manipulating yeast genome using plasmid vectors," Meth. Enzymol. 185:280-297, 1990.

Sturzebecher et al., "Dramatic enhancement of the catalytic activity of coagulation factor IXa by alcohols," FEBS Letters 412:295-300, 1997.

Tsang et al., "A factor IX mutation, verified by direct genomic sequencing, causes haemophilia B by a novel mechanism," EMBO J. 7:3009-3015, 1988.

Walter et al., "Successful expression of human factor IX following repeat administration of an adenoviral vector in mice," Proc. Natl. Acad. Sci. USA 93:3056-3061, 1996.

Wojcik et al., "Factor IX Zutphen: a $Cys^{18}$ —Arg mutation resultss in formation of a heterodimer with $\alpha_1$-microglobulin and the inability to form a calcium-induced conformation," Biochem. J. 311:753-759, 1995.

International Search Report, PCT/US 01/47276, European Patent Office, Jul. 15, 2002.

Written Opinion, U.S. International Preliminary Examining Authority, Dec. 21, 2004.

* cited by examiner

```
GAAGGGACCAGTTTCTTAACTGGAATTATTAGCTGGGGTGAAGAGTGTGCAATGAAAGGCAAATATGGAATATATACCAAGGTATCCCGG
---------+---------+---------+---------+---------+---------+---------+---------+---------+ 1350
CTTCCCTGGTCAAAGAATTGACCTTAATAATCGACCCCACTTCTCACACGTTACTTTCCGTTTATACCTTATATATGGTTCCATAGGGCC

 E  G  T  S  F  L  T  G  I  I  S  W  G  E  E  C  A  M  K  G  K  Y  G  I  Y  T  K  V  S [R]
                                                                              230      233

TATGTCAACTGGATTAAGGAAAAAACAAAGCTCACTTAA
---------+---------+---------+--------> 1389
ATACAGTTGACCTAATTCCTTTTTTGTTTCGAGTGAATT

 Y  V  N  W  I  K  E  K  T  K  L  1
234            239   241   243
```

MUTANT HUMAN FACTOR IX WITH AN INCREASED RESISTANCE TO INHIBITION BY HEPARIN

The present application is a U.S. National Phase Application of international application no. PCT/US01/47276, which was filed Nov. 13, 2001. That application claims benefit of priority of U.S. application Ser. No. 60/248,326, which was filed Nov. 14, 2000, which is incorporated herein by reference in its entirety.

FIELD OF THE INVENTION

The present invention provides methods and compositions for use in the treatment of blood coagulation disorders. More particularly, the present invention describes mutant human factor IX compositions for use in the therapeutic intervention of hemophilia B.

BACKGROUND OF THE INVENTION

Hemophilia B (also known as Christmas disease) is one of the most common inherited bleeding disorders in the world. It results in decreased in vivo and in vitro blood clotting activity and requires extensive medical monitoring throughout the life of the affected individual. In the absence of intervention, the afflicted individual may suffer from spontaneous bleeding in the joints, which produces severe pain and debilitating immobility; bleeding into muscles results in the accumulation of blood in those tissues; spontaneous bleeding in the throat and neck may cause asphyxiation if not immediately treated; bleeding into the urine; and severe bleeding following surgery, minor accidental injuries, or dental extractions also are prevalent.

To the extent that the present invention relates to intervention of blood clotting disorders, a brief discussion of the biological factors and/or mechanisms involved in blood clotting is warranted. A blood clot is essentially a gelatinous mass, which seals blood vessels that have sustained an injury. Conversion of fluid blood to a blood clot involves the conversion of soluble fibrinogen, which is present in plasma, to the insoluble gelatinous blood clot, composed primarily of cross-linked fibrin. The conversion of fibrinogen to fibrin is the primary end result of a multi-step process referred to as the blood coagulation cascade. This-cascade is a highly regulated process that involves the sequential proteolytic conversion of serine proteases from zymogen to active conformations, and subsequent formation of calcium-dependent phospholipid-bound enzyme complexes with specific protein cofactors. Normal in vivo blood coagulation at minimum requires the serine proteases factors II (prothrombin), VII, IX, X and XI (soluble plasma proteins); cofactors including the transmembrane protein tissue factor and the plasma proteins factors V and VIII; fibrinogen, the transglutaminase factor XIII, phospholipid (including activated platelets), and calcium. Additional proteins including kallikrein, high molecular weight kininogen, and factor XII are required for some in vitro clotting tests, and may play a role in vivo under pathologic conditions. The coagulation cascade is regulated by the thrombomodulin-protein C pathway, the fibrinolysis pathway, tissue factor pathway inhibitor, and the serpin antithrombin III. Importantly, the inhibition of several coagulation proteases by antithrombin III (including factor IXa) is markedly accelerated by the anticoagulant drug heparin, as well as structurally similar heparan sulfate on the endothelial surface.

Upon injury, thrombocytes, in the presence of von Willebrand Factor (a component of clotting Factor VIII), cling to the collagen of injured connective tissue by adhesion. The thrombocytes change their form and develop protrusions, and in addition to this, their outer membrane facilitates the adhesion of further thrombocytes. Thereafter, various substances are released from granula of these cells, which results in vessel constriction as well as accumulation and activation of other factors of plasma blood clotting.

In hemophilia, blood clotting is disturbed by a lack of certain plasma blood clotting factors. Hemophilia B is caused by a deficiency in factor IX that may result from either the decreased synthesis of the factor IX protein or a defective molecule with reduced activity. The treatment of hemophilia occurs by replacement of the missing clotting factor by exogenous factor concentrates highly enriched in factor IX. However, generating such a concentrate is fraught with technical difficulties as described below.

Factor IX, like other clotting factors, is naturally produced as a precursor molecule having an additional pre-pro-sequence at the N-terminus. The pre-pro-sequence represents a signal sequence that causes the oriented transport of this protein in the cell. When the pre-pro Factor DC protein is secreted from the cell the pre-sequence is cleaved. The pro-sequence consists of about 15 to 18 amino acids and serves as a recognition sequence in carboxylation of glutamic acid residues to 4-carboxy-L-glutamic acid. After successful carboxylation, the pro-sequence is also cleaved. If the pro-sequence is not cleaved or only incompletely cleaved, only low activity clotting factors result. Human factor IX has a molecular weight of about 55,000 Dalton; when its pro-sequence is present the molecular weight is increased by about 2000 Dalton.

Purification of factor IX from plasma almost exclusively yields active factor IX. However, such purification of factor IX from plasma is very difficult because factor IX is only present in low concentration in plasma [5 μg/mL; Andersson, *Thrombosis Research* 7: 451–459 (1975)]. Efforts to produce recombinant factor IX have led to products with only low levels of activity [Kaufman et al., *J. Biol Chem* 261: 9622–9628 (1986); Busby et al., *Nature* 316: 217–273 (1985); Rees et al., *EMBO J* 7: 2053–2061 (1988)]. This can be traced back to an incomplete cleavage of the pro-sequence [Meulien et al., *Prot Engineer* 3: 629–633 (1990)] because a mixture of recombinantly produced pro-factor IX and factor IX is present in cell supernatants.

The in vivo activity of exogenously generated factor IX is limited both by protein half-life and inhibitors of coagulation, including antithrombin III. An additional factor that limits the use of exogenously generated factor IX in an effective therapeutic protocol is that endogenous heparan sulfate/heparin greatly inhibits the activity of factor IX that is used in the existing therapies for hemophilia B.

Heparin can inhibit factor IXa activity in the intrinsic tenase complex (factor IXa-factor VIIIa) directly, or markedly accelerate inhibition of factor IXa by antithrombin III. Heparan sulfate, a chemically similar glycosaminoglycan to heparin, is expressed widely in the body including the endothelial surface, where it has been demonstrated to accelerate inhibition of coagulation proteases by antithrombin III. Similarly, it may directly inhibit intrinsic tenase activity at sites of injury, limiting the in vivo activity of factor IXa. Thus, a mutant factor IXa that is resistant to the effects of heparin/heparan sulfate and retains in vitro clotting activity may have enhanced in vivo activity. Similar protein engineering approaches have been used to enhance the therapeutic efficacy of other serine proteases, including improvement of the fibrin binding properties of tissue plasminogen activator by mutagenesis.

Thus, there is a need for mutant factor IX, which has a reduced affinity for heparin but retains it anti-clotting activity, and remains active when administered as part of a therapeutic regimen for hemophilia B.

SUMMARY OF THE INVENTION

The present invention provides novel mutant forms of factor IX that may be used in the therapeutic intervention of hemophilia B. In a preferred embodiment, the present invention provides a mutant human factor IX comprising a mutation in the heparin binding domain of factor IX, which decreases its affinity for heparin, as compared to wild-type human factor IX. By heparin binding domain, the present invention refers to that site on the factor IX protein that binds to and interacts with heparin. In more specific embodiments, the mutation is a mutation of the amino acid residue 233, 230, 239, 241, 87, 91, 98, 101, or 92 of wild-type human factor IX. In preferred embodiments, it is contemplated that one or more of these residues is mutated. In additional embodiments, it is contemplated that the mutation further comprises a substitution of arginine 170 of the wild-type human factor IX for an alanine. The numbering system employed herein is the chymotrypsin numbering system well known to those of skill in the art [Bajaj and Birktoft, Meth Enzymol 222:96–128 (1993)] and is also depicted herein in FIG. 3.

A preferred mutant human factor IX of the present invention has a mutation of the amino acid located at residue number 233 of wild-type human factor IX, wherein said mutation decreases the affinity of said mutant human factor IX for heparin as compared to wild-type human factor IX. More particularly, the mutation is a substitution of the arginine at position 233 to any other amino acid. In still more specific embodiments, it is contemplated that the arginine at position 233 is substituted with an alanine. Alternatively, the arginine at 233 or any other arginine in the heparin binding domain is replaced with a glutamate.

Another aspect of the present invention describes a method of treating a subject having hemophilia comprising administering to said subject a composition comprising a mutant human factor IX of the present invention, in an amount effective to promote blood clotting in said subject. Further methods contemplate administering to the subject a composition comprising one or more additional blood clotting factors other than said mutant human factor IX. In particular embodiments, the subject suffering from hemophilia is suffering from hemophilia B.

Additional methods of treating hemophilia in a mammal also are contemplated. Such methods comprise providing an expression construct comprising a polynucleotide encoding a mutant factor IX of the present invention, operably linked to a promoter; and administering in a mammal an amount of the expression construct effective to allow the mutant factor IX to be expressed at levels having a therapeutic effect on the mammal. The indicia of a therapeutic effect of a given hemophilia therapy are well known to those of skill in the art. For example, in the present invention, the therapeutic effect is an increased resistance of factor IX to inhibition by heparin. More particularly, the therapeutic effect is a decrease in the blood clotting time of said mammal as compared to the blood clotting time of said mammal in the absence of said expression construct. In preferred aspects the expression construct comprises a viral vector selected from the group consisting of an adenovirus, an adeno-associated virus, a retrovirus, a herpes virus, a lentivirus and a cytomegalovirus. In preferred embodiments, the expression control element is selected from the group consisting of a cytomegalovirus immediate early promoter/enhancer, a skeletal muscle actin promoter and a muscle creatine kinase promoter/enhancer.

In specific embodiments, it is contemplated that the therapeutic compositions (protein or expression vector compositions) of the present invention are administered to at least two sites in the mammal.

Yet another aspect of the present invention contemplates a recombinant host cell stably transformed or transfected with a polynucleotide encoding a mutant human factor IX of the present invention in a manner allowing the expression in the host cell of said mutant human factor IX. In specific embodiments, such a recombinant host cell may be employed in methods of for the large scale production of the mutant human factor IX protein.

Also contemplated by the present invention are pharmaceutical compositions comprising a mutant human factor IX protein of the present invention and a pharmaceutically acceptable carrier, excipient or diluent. Also contemplated are pharmaceutical compositions comprising an expression construct comprising a vector having an isolated polynucleotide encoding a mutant human factor IX of the instant invention and a promoter operably linked to said polynucleotide; and a pharmaceutically acceptable carrier, excipient or diluent. It is contemplated that in addition to the mutant human factor IX, the pharmaceutical compositions may comprise additional therapeutic components such as for example, other blood clotting factors and hemophilia therapeutic compositions.

Other aspects, features and advantages of the present invention will be apparent from the detailed description. It should be understood that the detailed description presented below, while providing preferred embodiments of the invention, is intended to be illustrative only since changes and modification within the scope of the invention will be possible whilst still providing an embodiment that is within the spirit of the invention as a whole.

BRIEF DESCRIPTION OF THE DRAWINGS

The following drawings form part of the present specification and are included to further demonstrate aspects of the present invention. The invention may be better understood by reference to one or more of the drawings in combination with the detailed description of the specific embodiments presented herein.

FIG. 3A through FIG. 3C. Contiguous DNA (SEQ ID NO: 1) and amino acid (SEQ ID NO: 2) sequences of factor IX, including bold numbers underneath, designating the amino acid sequence corresponding to the chymotrypsin numbering system.

DETAILED DESCRIPTION OF THE PREFERRED EMBODIMENTS

Hemophilia B is one of the most prevalent blood clotting disorders and results from a deficiency of or defect in endogenous factor IX gene expression or activity, respectively. Therapeutic intervention requires replacement therapy in which the patient is provided with exogenous factor IX. However, treatment is limited by the commercial availability of clotting factor and the expense of treatment. Further, factor IX that is isolated from natural sources or that is produced recombinantly using native sequences is inhibited by endogenous heparin/heparan sulfate in both an antithrombin III-dependent and independent manner, limiting in vivo activity and half-life of activated factor IXa. Hence the presently available replacement therapies are ineffective at providing an adequate remedy for the disease.

Figure 3A:
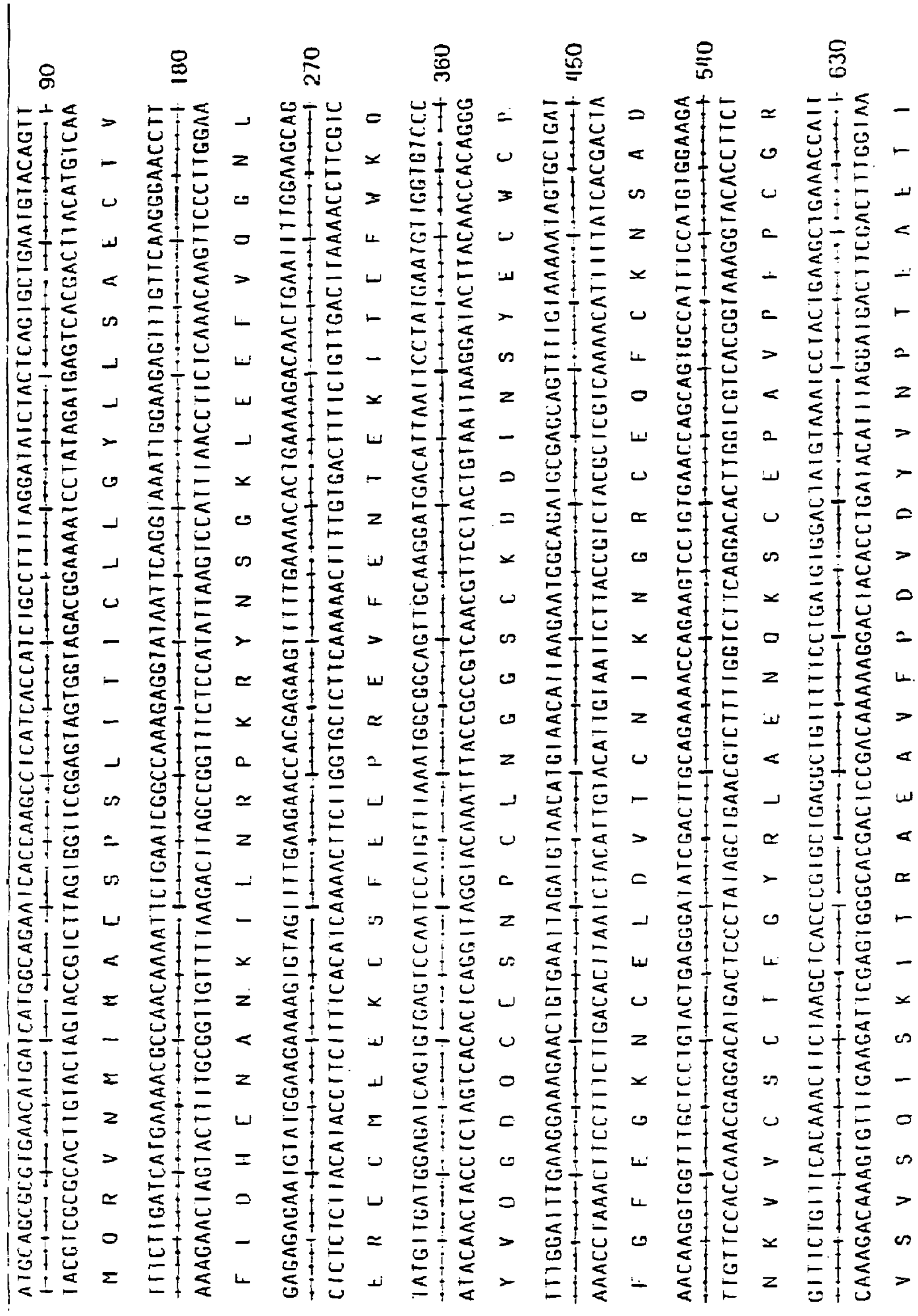
Figure 3B:
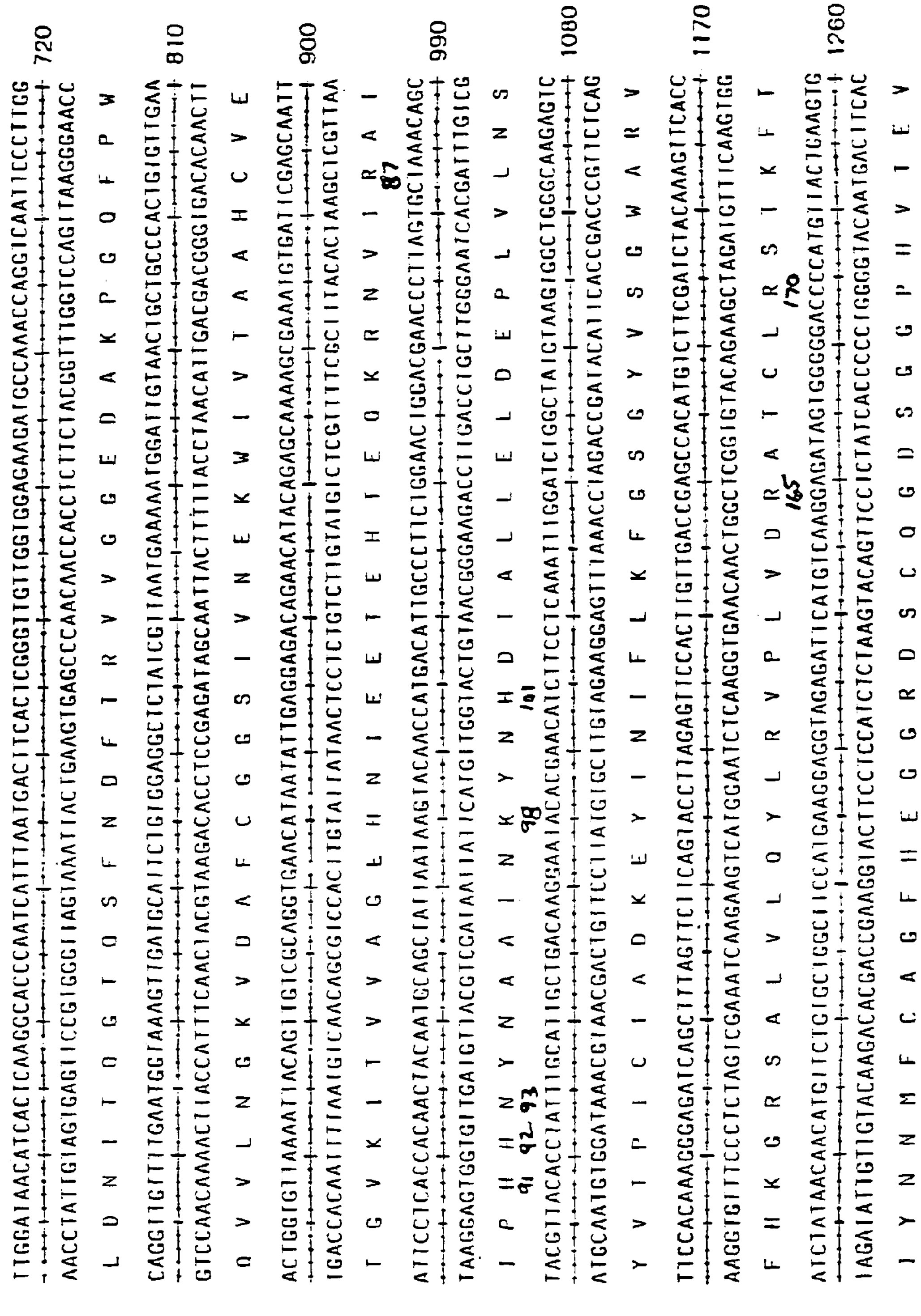

The present invention describes a mutant human factor IX that has an increased resistance to heparin inhibition in vitro as compared to wild-type human factor IX. More particularly, the invention describes a mutant factor IX that has an Arg to Ala substitution at residue 233 (according to the chymotrypsin numbering system, see FIG. 3, and SEQ ID NO: 2). The increased resistance of this mutant human factor IX to heparin means that the mutant human factor IX is a more effective replacement therapy for patients suffering from hemophilia B than administering wild-type factor IX. Further, it is expected that this mutant human factor IX also may possess an increased in vivo blood clotting activity as compared to wild-type human factor IX. Methods and compositions for exploiting the therapeutic potential of these findings are discussed in further detail herein below.

A. Role of Factor IX in the Blood Coagulation Cascade.

Factor IX is a key serine protease that participates in the middle phase of the blood clotting cascade. Factor IX is activated by either factor XIa or by factor VIIa-tissue factor in a $Ca^{2+}$ dependent manner. The activated factor IXa with its cofactor VIIIa, in the presence of $Ca^{2+}$ and phospholipid, forms the intrinsic tenase complex and is responsible for generating activated Factor X. Factor IX is functionally deficient or absent in individuals with the inherited disorder hemophilia B.

Ex vivo modeling of blood coagulation demonstrates that formation of the membrane bound intrinsic tenase (factor IXa-factor VIIIa) and prothrombinase (factor Xa-factor Va) complexes results in a localized, explosive increase in thrombin generation [Lawson et al., *J Biol Chem.,* 269(37): 23357–66 (1994); Rand et al., *Blood,* 88(9):3432–45 (1996)]. In minimally altered whole blood, the rate limiting factor for thrombin generation is the activation of factor Xa by the intrinsic tenase complex [Rand et al., *Blood,* 88(9): 3432–45 (1996)]. In a cell-based system containing platelets and monocytes expressing tissue factor, addition of picomolar factor IXa generates significantly more thrombin than similar concentrations of factor Xa [Hoffman et al., *Blood,* 86(5): 1794–801 (1995)]. Omitting either factor IX or factor VIII markedly reduces the generation of thrombin [Lawson et al., *J Biol Clem,* 269(37): 23357–66(1994)]. Thus, formation and activity of the intrinsic tenase complex is critical to the final rate of thrombin generation during the propagation phase of coagulation. The activity of the intrinsic tenase complex appears to be primarily regulated by instability (loss of the A2 domain) and proteolytic inactivation of factor VIIIa (by factor IXa) [Fay et al., *J Biol Chem,* 271(11): 6027–32 (1996)]. The pivotal role of intrinsic tenase suggests that regulation of this enzyme complex is critical to maintaining hemostatic balance.

Heparin has anticoagulant effects prolongation of in vitro coagulation assays) in plasma which are antithrombin (ATIII) dependent, largely attributed to the acceleration of factor Xa and thrombin inhibition [Hirsh et al., *Chest* 108(4 Suppl) (1995)]. In both the purified state and in plasma, ATIII inhibits factor IXa at a significantly slower baseline rate than thrombin and factor Xa [Jordan et al., *J Biol Chem,* 255(21):10081–90 (1980); Pieters et al., *J Biol Chem,* 263 (30):15313–8 (1988); Pieters et al., *Blood,* 76(3): 549–54 (1990)]. However, addition of unfractionated heparin to contact-activated plasma results in a significant increase in the amount of factor IXa-antithrombin complex formed [McNeely and Griffith, *Blood,* 65(5): 1226–31 (1985)]. Similar to thrombin, heparin acceleration of factor IXa inhibition by antithrombin demonstrates a biphasic dose response, and requires high molecular weight oligosaccharides for optimal rate enhancement [Holmer et al., *Biochem J,* 193(2): 395–400 (1981); Mauray et al., *Biochim Biophys Acta,* 1387(1–2): 184–94 (1998)]. These results suggest a template mechanism for heparin catalysis, in which inhibition is accelerated by the binding of protease and inhibitor to the same oligosaccharide chain.

In addition to accelerating protease inhibition by ATIII, heparin also inhibits the intrinsic tenase complex in an a ATIII independent manner [Barrow et al., *J Biol Chem,* 269(43): 26796–800 (1994)]. This inhibition exhibits a partial, noncompetitive pattern, which is not explained by effects on cofactor stability or assembly of the factor IXa-factor VIIIa complex [Barrow et al., *J Biol Chem,* 269(43): 26796–800 (1994)]. By eliminating potential effects on assembly or stability of the complex that would reduce the effective enzyme concentration, these results suggest that heparin directly modulates the catalytic activity of the enzyme complex [Barrow et al., *J Biol Chem,* 269(43): 26796–800 (1994)]. From mechanistic studies the inventor has inferred a model in which heparin binds to a regulatory site on factor IX. The inventor has shown that site directed mutagenesis of the heparin binding domain (at position R233) generated a mutant human factor IX, which when compared to wild-type factor IX, demonstrated markedly reduced inhibition by heparin. This mutant human factor IX as well as other mutant human factor IX proteins in which the regulatory site that binds heparin has been disrupted will be useful in replacement therapy for individuals suffering from hemophilia.

The amino acid structure of human factor DC is well known to those of skill in the art, see Bajaj and Birktoft [*Meth Enzymol,* 222: 96–128 (1993)]. Given that the instant invention has shown that it is possible to generate such a mutant, those of skill in the art will be able to produce other mutants having a similar activity. Similarly, the nucleic acid sequence of the gene encoding factor IX also is well known to those of skill in the art (see FIG. 3 and SEQ ID NO: 1).

Of additional interest, recent studies have shown that the endocytic receptor low density lipoprotein receptor-related protein (LRP) was demonstrated to bind factor IXa upon activation from a zymogen form in a two-site binding model with equilibrium dissociation constants of 27 nM and 69 nM [eels et al., *Blood* 96(10): 3459–3465 (2000)]. Modification of the factor IXa active site, however, did not affect binding to LRP, suggesting that binding of factor IXa to LRP involves an enzyme exosite. LRP-deficient cells degrade 35% less factor IXa than LRP-expressing cells, suggesting a role for LRP in the transport of factor IXa to the intracellular degradation pathway. Degradation of factor IXa by proteoglycan-deficient cells proceeded at a rate lower than 83% than that of wild-type cells, also suggesting a role for proteoglycans in the binding to LRP. Furthermore, the binding of factor IXa to LRP can be fully inhibited in the presence of either 100 U/mL unfractionated or low molecular weight heparin. In contrast, little, if any, inhibition was observed in the presence of 100-μg/mL chondroitin sulfate. These data indicate that the heparin-binding domain of factor IXa may contribute to the interaction with LRP. Thus, factor IXa proteins with reduced affinity for heparin may have reduced clearance by LRP-dependent mechanisms, further enhancing their in vivo activity.

B. Mutant Factor IX

The present invention contemplates the production of mutant human coagulation factor IX that has an increased resistance to inhibition by heparin/heparan sulfate by both antithrombin-dependent and independent mechanisms. By mutant human factor IX, the present invention means human factor IX in which the wild-type sequence has been mutated.

Specifically contemplated by the present invention is site-specific mutagenesis of wild-type human factor IX. While the amino acid sequence variants of the polypeptide can be substitutional mutants in which the amino acid at a given site is substituted for another, insertional or deletion variants also are contemplated.

Substitutional variants typically exchange one amino acid of the wild-type for another at one or more sites within the protein, and may be designed to modulate one or more properties of the polypeptide, such as stability against proteolytic cleavage, without the loss of other functions or properties. Substitutions of amino acids to maintain activity or properties preferably are conservative, that is, one amino acid is replaced with one of similar shape and charge.

Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in the Table A (from WO 97/09433, page 10, published Mar. 13, 1997 (PCT/GB96/02197, filed Sep.6, 1996), immediately below.

TABLE A

Conservative Substitutions I

| SIDE CHAIN CHARACTERISTIC | AMINO ACID |
|---|---|
| Aliphatic | |
| Non-polar | G A P |
| | I L V |
| Polar - uncharged | C S T M |
| | N Q |
| Polar - charged | D E |
| | K R |
| Aromatic | H F W Y |
| Other | N Q D E |

Alternatively, conservative amino acids can be grouped as described in Lehninger. [*Biochemistry*, Second Edition; Worth Publishers, Inc. NY:NY (1975), pp.71–77] as set out in Table B, immediately below.

TABLE B

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still an another alternative, exemplary conservative substitutions are set out in Table C, immediately below.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |

TABLE C-continued

| Conservative Substitutions III | |
|---|---|
| Original Residue | Exemplary Substitution |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

Also contemplated are non-conservative substitutions, in which an amino acid is replaced with one of different properties. Replacement of arginine or lysine to glutamate (charge reversal) to disrupt the electrostatic binding of the protease to heparin, similar to the strategy used for thrombin-heparin binding, is an example of such non-conservative substitutions [Sheehan and Sadler, *Proc Nat'l Acad Sci USA,* 91(12): 5518–22 (1994)]. Such nonconservative mutations may be useful in generating further mutants that have increased resistance to heparin inhibition.

The binding of polyanionic heparin chains to factor IX(a) likely involves interactions with basic amino acid residues on the protease surface. The binding of heparin to thrombin, a homologous coagulation protease, is a highly electrostatic interaction that involves a number of basic residues in exosite II [Sheehan and Sadler, *Proc Nat'l Acad Sci USA,* 91(12): 5518–22 (1994); Olson et al., *J Biol Chem;* 266(10): 6342–52 (1991)]. The inventor prepared a three-dimensional structure of human factor Ixa by homology using SWISS-MODEL. Based on homology to the thrombin-heparin interaction, basic surface residues (lysine, arginine, or histidine) in the carboxyl-terminus -helix, and the insertion loop 80–90 (chymotrypsin numbering) are appropriate targets for mutagenesis. Candidate residues include R87, H91, H92, K98, H101 in the 80–90 loop region, and K230, R233, K239, and K241 in the carboxyl-terminus helix. It is expected that these mutations will be within the heparin binding domain of factor IX. Preferred mutants include single amino acid substitutions of alanine for R87, H92, R233, H101, and K241. Other residues are those that are within about 5Å that interact with these aforementioned residues. The mutations may be combined with a substitution of R170 to A170 [Chang et al., *J Biol Chem,* 273(20): 12089–94 (1998)]. Of course these residues could also be mutated to any other residue if desired, so long as the mutation provided a mutant human factor IX that was resistant to inhibition by heparin. In other preferred aspects, such a mutant human factor IX also retains blood coagulation activity. Using such mutagenesis also will allow mapping of the heparin binding site, similar to the mapping studies performed for thrombin [Sheehan and Sadler, *Proc Nat'l Acad Sci USA,* 91(12): 5518–22 (1994)]. Further it is contemplated that mutations may be combined to provide a more dramatic effect on heparin binding and function.

A preferred embodiment of the present invention contemplates generating a mutation of the arginine at 233. This arginine may be mutated to any amino acid. It should be noted that the mutants of the factor Ix peptide should have an increased resistance to heparin inhibition. Such mutants also may preferably possess an increased clotting activity.

In order to construct mutants such as those described above, one of skill in the art may employ well known standard technologies. Proteins expressed from such mutant can be assayed for appropriate heparin inhibition and/or effect on blood clotting as described in further detail below.

A random insertional mutation may also be performed by cutting the DNA sequence with a DNase I, for example, and inserting a stretch of nucleotides that encode, 3, 6, 9, 12 etc., amino acids and religating the end. Once such a mutation is made the mutants can be screened for various activities presented by the wild-type protein.

Point mutagenesis also may be employed to identify with particularity the amino acid residues that are important in particular activities associated with the heparin binding of factor IX. Thus, one of skill in the art will be able to generate single base changes in the DNA strand to result in an altered codon and a missense mutation.

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the nucleotide(s) being mutated. Typically, a primer of about 17 to 25 nucleotides in length is preferred, with about 5 to about 10 matching bases on both sides of the nucleotide(s) being altered.

The technique typically employs a bacteriophage vector that exists in both a single-stranded and double-stranded form. Typical vectors useful in site-directed mutagenesis include vectors such as the M13 phage. These phage vectors are commercially available and their use is generally well known to those skilled in the art. Double-stranded plasmids also are routinely employed in site-directed mutagenesis, which eliminates the step of transferring the gene of interest from a phage to a plasmid.

In general, site-directed mutagenesis is performed by first obtaining a single-stranded vector, or melting of two strands of a double-stranded vector, which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

A PCR-based method for site-directed mutagenesis is particularly preferred. Overlapping forward (positive strand) and reverse (negative strand) primers containing the desired mutation and 10–15 matching nucleotides flanking both sides, are annealed with the denatured wild-type cDNA in a suitable plasmid vector (i.e. Bluescript®). This template is then subject to amplification by PCR with a high fidelity thermostable DNA polymerase, the product digested with the restriction endonuclease Dpn I (to degrade the methylated parental or wild-type plasmid), and resulting DNA employed for transformation of bacteria. Antibiotic resistant bacterial colonies (containing the plasmid) are then selected for overnight growth, isolation of plasmid DNA (miniprep), and sequencing to confirm the presence of the mutation.

C. Recombinant Protein Production.

Given the above disclosure of mutant human factor IX peptides it will be possible for one of skill in the art to produce human factor IX peptides by automated peptide synthesis, by recombinant techniques or both.

The mutant factor IX protein of the invention can be synthesized in solution or on a solid support in accordance with conventional techniques. Various automatic synthesizers are commercially available and can be used in accordance with known protocols. See, for example, Stewart and Young, Solid Phase Peptide Synthesis, 2d. ed., Pierce Chemical Co., (1984); Tam et al., *J Amer Chem Soc,* 105: 6442 (1983); Merrifield, *Science,* 232: 341–347 (1986); and Barany and Merrifield, *The Peptides,* Gross and Meienhofer, eds, Academic Press, New York, 1–284 (1979), each incorporated herein by reference. The active protein can be readily synthesized and then screened in screening assays designed to identify reactive peptides.

Alternatively, a variety of expression vector/host systems may be utilized to contain and express a mutant factor IX coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the protein are described herein below.

A yeast system may be employed to generate the mutant peptides or proteins of the present invention. The coding region of the mutant factor IX cDNA is amplified by PCR. A DNA encoding the yeast pre-pro-alpha leader sequence is amplified from yeast genomic DNA in a PCR reaction using one primer containing nucleotides 1–20 of the alpha mating factor gene and another primer complementary to nucleotides 255–235 of this gene [Kurjan and Herskowitz, *Cell,* 30: 933–943 (1982)]. The pre-pro-alpha leader coding sequence and mutant factor IX coding sequence fragments are ligated into a plasmid containing the yeast alcohol dehydrogenase (ADH2) promoter, such that the promoter directs expression of a fusion protein consisting of the pre-pro-alpha factor fused to the mature mutant factor IX polypeptide. As taught by Rose and Broach [*Meth Enzymol,* 185: 234–279, D. Goeddel, ed., Academic Press, Inc., San Diego, Calif. (1990)], the vector further includes an ADH2 transcription terminator downstream of the cloning site, the yeast "2-micron" replication origin, the yeast leu-2d gene, the yeast REP1 and REP2 genes, the *E. coli* beta-lactamase gene, and an *E. coli* origin of replication. The beta-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells, using a known method, e.g., lithium acetate treatment [Stearns et al., *Meth Enzymol,* 185: 280–297 (1990)]. The ADH2 promoter is induced upon exhaustion of glucose in the growth media [Price et al., *Gene,* 55: 287 (1987)]. The pre-pro-alpha sequence effects secretion of the fusion protein from the cells. Concomitantly, the yeast KEX2 protein cleaves the pre-pro sequence from the mature mutant factor IX [Bitter et al., *Proc Nat'l Acad Sci USA,* 81: 5330–5334 (1984)].

Alternatively, mutant factor IX may be recombinantly expressed in yeast using a commercially available expression system, e.g., the Pichia Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol.

The secreted mutant human factor IX is purified from the yeast growth medium by, e.g., the methods used to purify mutant factor IX from bacterial and mammalian cell supernatants.

Alternatively, the cDNA encoding mutant factor IX may be cloned into the baculovirus expression vector pVL1393 (PharMingen, San Diego. Calif.). This mutant factor IX-containing vector is then used according to the manufacturer's directions (PharMingen) to infect *Spodoptera frugiperda* cells in sF9 protein-free media and to produce recombinant protein. The protein is purified and concentrated from the media using a heparin-Sepharose column (Pharmacia, Piscataway, N.J.) and sequential molecular sizing columns (Amicon, Beverly, Mass.), and resuspended in PBS. SDS-PAGE analysis shows a single band and confirms the size of the protein, and Edman sequencing on a Porton 2090 Peptide Sequencer confirms its N-terminal sequence.

Alternatively, the mutant factor IX may be expressed in an insect system. Insect systems for protein expression are well known to those of skill in the art. In one such system, Autographa californica nuclear polyhedrosis virus (AcNPV) is used as a vector to express foreign genes in *Spodoptera frugiperda* cells or in Trichoplusia larvae. The mutant factor IX coding sequence is cloned into a nonessential region of the virus, such as the polyhedrin gene, and placed under control of the polyhedrin promoter. Successful insertion of mutant factor IX will render the polyhedrin gene inactive and produce recombinant virus lacking coat protein coat. The recombinant viruses are then used to infect *S. frugiperda* cells or *Trichoplusia* larvae in which mutant factor IX is expressed [Smith et al., *J Virol,* 46: 584 (1983); Engelhard et al., *Proc Nat'l Acad Sci USA,* 91: 3224–7 (1994)].

In another example, the DNA sequence encoding the mature form of the protein is amplified by PCR and cloned into an appropriate vector for example, pGEX-3X (Pharmacia, Piscataway, N.J.). The pGEX vector is designed to produce a fusion protein comprising glutathione-S-transferase (GST), encoded by the vector, and a protein encoded by a DNA fragment inserted into the vector's cloning site. The primers for the PCR may be generated to include, for example, an appropriate cleavage site.

The recombinant fusion protein may then be cleaved form the GST portion of the fusion protein. The pGEX-3X/mutant human factor IX construct is transformed into *E. coli* XL-1 Blue cells (Stratagene, La Jolla Calif.), and individual transformants were isolated and grown. Plasmid DNA from individual transformants is purified and partially sequenced using an automated sequencer to confirm the presence of the desired mutant human factor IX encoding gene insert in the proper orientation.

While certain embodiments of the present invention contemplate producing the mutant human factor IX protein using synthetic peptide synthesizers and subsequent FPLC analysis and appropriate refolding of the cysteine double bonds, it is contemplated that recombinant protein production also may be used to produce the mutant human factor IX peptide compositions. For example, induction of the GST/mutant human factor IX fusion protein is achieved by growing the transformed XL-1 Blue culture at 37° C. in LB medium (supplemented with carbenicillin) to an optical density at wavelength 600 nm of 0.4, followed by further incubation for 4 hours in the presence of 0.5 mM Isopropyl β-D-Thiogalactopyranoside (Sigma Chemical Co., St. Louis Mo.).

The fusion protein, expected to be produced as an insoluble inclusion body in the bacteria, may be purified as follows. Cells are harvested by centrifugation; washed in 0.15 M NaCl, 10 mM Tris, pH 8, 1 mM EDTA; and treated with 0.1 mg/mL lysozyme (Sigma Chemical Co.) for 15 minutes at room temperature. The lysate is cleared by sonication, and cell debris is pelleted by centrifugation for 10 minutes at 12,000 X g. The fusion protein-containing pellet is resuspended in 50 mM Tris, pH 8, and 10 mM EDTA, layered over 50% glycerol, and centrifuged for 30 min. at 6000 X g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/mutant human factor IX fusion protein is produced in bacteria as a soluble protein, it may be purified using the GST Purification Module (Pharmacia Biotech).

The fusion protein may be subjected to digestion to cleave the GST from the mature mutant human factor IX protein. The digestion reaction (20–40 μg fusion protein, 20–30 units human thrombin [4000 U/mg (Sigma) in 0.5 mL PBS] is incubated 16–48 hrs, at room temperature and loaded on a denaturing SDS-PAGE gel to fractionate the reaction products. The gel is soaked in 0.4 M KCl to visualize the protein bands. The identity of the protein band corresponding to the expected molecular weight of mutant human factor IX may be confirmed by partial amino acid sequence analysis using an automated sequencer (Applied Biosystems Model 473A. Foster City, Calif.).

Alternatively, the DNA sequence encoding the predicted mature mutant human factor IX protein may be cloned into a plasmid containing a desired promoter and, optionally, a leader sequence, see, for example, [Better et al., *Science,* 240: 1041–43 (1988)]. The sequence of this construct may be confirmed by automated sequencing. The plasmid is then transformed into *E. coli* strain MC1061 using standard procedures employing $CaCl_2$ incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will affect secretion of the mature mutant human factor IX protein and be cleaved during secretion.

The secreted recombinant protein is purified from the bacterial culture media by the method described herein below.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing, which cleaves a "prepro" form of the protein, may also be important to correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In a particularly preferred method of recombinant expression of the mutant human factor IX proteins of the present invention 293 cells are co-transfected with plasmids containing the mutant human factor IX cDNA in the pCMV vector (5' CMV promoter, 3' HGH poly A sequence) and pSV2neo (containing the neo resistance gene) by the calcium phosphate method. Preferably, the vectors should be linearized with ScaI prior to transfection. Similarly an alternative construct using a similar pCMV vector with the neo gene incorporated can be used. Stable cell lines are selected from single cell clones by limiting dilution in growth media containing 0.5 mg/mL G418 (neomycin like antibiotic) for 10–14 days. Cell lines are screened for mutant factor IX expression by ELISA or Western blot, and high expressing cell lines are expanded for large scale growth.

It is preferable that the transformed cells are used for long-term, high-yield protein production and as such stable expression is desirable. Once such cells are transformed with vectors that contain selectable markers along with the desired expression cassette, the cells may be allowed to grow for 1–2 days in an enriched media before they are switched to selective media. The selectable marker is designed to confer resistance to selection and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to methotrexate; gpt, that confers resistance to mycophenolic acid; neo, that confers resistance to the aminoglycoside G418; also that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, β-glucuronidase and its substrate, GUS, and luciferase and its substrate, luciferin.

D. Protein Purification

It will be desirable to purify the mutant factor IX proteins generated by the present invention. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; and isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE [Capaldi et al., *Biochem Biophys Res Comm,* 76: 425 (1977)]. It will therefore be appreciated that under differing electrophoresis conditions, the apparent molecular weights of purified or partially purified expression products may vary.

In particular, the present invention incorporates herein by reference U.S. Pat. No. 6,063,909; U.S. Pat. No. 6,034,222; U.S. Pat. No. 5,639,857 (each incorporated herein by reference). These documents describe specific exemplary methods for the isolation and purification of factor IX compositions that may be useful in isolating and purifying the mutant human factor IX of the present invention. Given the disclosure of these patents, it is evident that one of skill in the art would be well aware of numerous purification techniques that may be used to purify factor IX from a given source.

U.S. Pat. No. 6,063,909 provides methods and compositions for protecting blood coagulation factor IX from proteases during purification or storage. Such methods employ high concentrations of one or more water soluble organic or inorganic salts to stabilize factor IX against conversion to clinically unacceptable peptide structures such as factor IXa, and/or degraded factor IX peptides. The technique is useful in stabilizing intermediate purity factor IX preparations during purification, and in maintaining the integrity of purified factor IX during long term storage. One of skill in the art may use methods such as those disclosed in U.S. Pat. No. 6,063,909 in combination with the instant invention to provide additional stability to the factor IX preparations of the present invention.

U.S. Pat. No. 6,034,222 describes a method for the chromatographic separation of recombinant pro-factor IX from recombinant factor IX, which employs ion exchangers such as QAE (QAE-Sephadex®, a strong basic anion exchanger comprised of dextran gels that are modified by introduction of N,N-diethyl-N-(2-hydroxy-1-propyl)-ammonio-ethyl groups), DEAE (DEAE cellulose, diethylaminoethyl cellulose, anion exchanger) or TMAE (TMAE cellulose, triethylammonioethyl cellulose) and subsequent elution of factor IX by buffer solutions with high salt concentrations and/or low pH values.

Yet another method for the purification of mutant factor IX contemplates the use of immunoaffinity chromatography using an immunoadsorbent comprising a monoclonal antibody. See, for example, [Liebman et al. *Blood,* 62(5), supp. 1, 288a (1983); Liebman et al., *Proc Nat'l Acad Sci USA,* 82: 3879–3883 (1985); Bessos, *Thrombosis and Haemostasis,* 56(1): 86–89 (1986)]. U.S. Pat. No. 5,614,500 describes an immunoaffinity purification of factor IX conducted in the presence of a chelating agent. The techniques described therein may be useful in the present invention.

Also it is contemplated that a combination of anion exchange and immunoaffinity chromatography may be employed to produce purified mutant factor IX compositions of the present invention.

In a particularly preferred protocol for protein purification, serum free media containing 10 μg/mL Vitamin K is incubated with a confluent cell line expressing the mutant human factor IX protein, and harvested every 48 hrs for 10 days. Benzamidine (5 mM) is added, the media centrifuged at 1200 g to eliminate cellular and particulate debris, and the conditioned media frozen at −25° C. Upon thawing, the conditioned media is pooled, filtered, and subjected to barium chloride precipitation [Cote et al., *J Biol Chem,* 269(15): 11374–80 (1994)]. The precipitate is dissolved in 0.2 M EDTA, and the eluate dialyzed overnight before application to a Mono Q HR 5/5 column(0.15 M NaCl, 20 mM HEPES, pH 7.4, 0.1% PEG-8000). Human factor IX is eluted with a calcium chloride gradient (0–45 mM) and concentrated in a Centricon-30. This approach selects for fully gamma-carboxylated factor IX based on the specificity of the calcium chloride elution. Since this purification takes advantage of the unique properties of the Gla domain, mutations introduced into the protease domain are not expected to affect purification of the proteins.

E. Vectors for Cloning, Gene Transfer and Expression.

As discussed in the previous section, expression vectors are employed to express the mutant human factor IX polypeptide product, which can then be purified and used in replacement therapy for the treatment of hemophilia B. In other embodiments, expression vectors may be used in gene therapy applications to introduce the mutant factor IX-encoding nucleic acids into cells in need thereof and/or to induce mutant factor IX expression in such cells. The present section is directed to a description of the production of such expression vectors.

Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are described. The conditions for the use of a number of dominant drug selection markers for establishing permanent, stable cell clones expressing the products also are provided, as is an element that links expression of the drug selection markers to expression of the polypeptide.

a. Regulatory Elements.

Promoters and Enhancers. Throughout this application, the term “expression construct” or “expression vector” is meant to include any type of genetic construct containing a nucleic acid coding for gene products in which part or all of the nucleic acid encoding sequence is capable of being transcribed. The transcript may be translated into a protein, but it need not be In certain embodiments, expression includes both transcription of a gene and translation of mRNA into a gene product. The nucleic acid encoding a gene product is under transcriptional control of a promoter. A “promoter” refers to a DNA sequence recognized by the synthetic machinery of the cell, or introduced synthetic machinery, required to initiate the specific transcription of a gene. The phrase “under transcriptional control” means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest. The use of other viral or mammalian cellular or bacterial phage promoters that are well-known in the art to achieve expression of a coding sequence of interest is contemplated as well, provided that the levels of expression are sufficient for a given purpose. By employing a promoter with well known properties, the level and pattern of expression of the protein of interest following transfection or transformation can be optimized.

Selection of a promoter that is regulated in response to specific physiologic or synthetic signals can permit inducible expression of the gene product. Several inducible promoter systems are available for production of viral vectors. One such system is the ecdysone system (Invitrogen, Carlsbad. Calif.), which is designed to allow regulated expression of a gene of interest in mammalian cells. It consists of a tightly regulated expression mechanism that allows virtually no basal level expression of the transgene, but over 200-fold inducibility.

Another inducible system that would be useful is the Tet-Off™ or Tet-On™ system (Clontech, Palo Alto, Calif.) originally developed by Gossen and Bujard [*Proc Nat'l Acad Sci USA,* 15;89(12):5547–51 (1992); Gossen et al., *Science,* 268(5218): 1766–69 (1995)].

In some circumstances, it may be desirable to regulate expression of a transgene in a gene therapy vector. For example, different viral promoters with varying strengths of activity may be utilized depending on the level of expression desired. In mammalian cells, the CMV immediate early promoter is often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly, tissue specific promoters may be used to affect transcription in specific tissues or cells to reduce potential toxicity or undesirable effects on non-targeted tissues. For example, promoters such as the PSA, probasin, prostatic acid phosphatase, or prostate-specific glandular kallikrein (hK2) may be used to target gene expression in the prostate.

In certain indications, it may be desirable to activate transcription at specific times after administration of the gene therapy vector. This may be done with such promoters as those that are hormone or cytokine regulatable. For example, in gene therapy applications where the indication is a gonadal tissue where specific steroids are produced or routed to, use of androgen or estrogen regulated promoters may be advantageous. Such promoters that are hormone regulatable include MMTV. MT-1, ecdysone, and RuBisco. Other hormone regulated promoters such as those responsive to thyroid, pituitary, and adrenal hormones are expected to be useful in the present invention. Cytokine and inflammatory protein responsive promoters that could be used include K and T Kininogen [Kageyama et al., *J Biol Chem,* 262(5): 2345–51 (1987)], c-fos, TNF-alpha, C-reactive protein [Arcone et al., *Nucl Acids Res* 16(8): 3195–207 (1988)], haptoglobin [Oliviero et al., *EMBO J,* 6(7): 1905–12 (1987)], serum amyloid A2, C/EBP alpha, IL-1, IL-6 [Poli and Cortese, *Proc Nat'l Acad Sci USA,* 86(21): 8202–6 (1989)], complement C3 [Wilson et al., *Mol Cell Biol* 10(12): 6181–91 (1990)], IL-8, alpha-1 acid glycoprotein [Prowse and Baumann, *Mol Cell Biol,* 8(1): 42–51 (1988)], alpha-1 antitypsin, lipoprotein lipase [Zechner et al., *Mol Cell Biol,* 8(6): 2394–401 (1988)], angiotensinogen [Ron et al., *Mol Cell Biol* 11(5): 2887–95 (1991)], fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), stromelysin (inducible by phorbol ester, interleukin-1 and EGF), alpha-2 macroglobulin, and alpha-1 antichymotrypsin.

Other promoters that could be used according to the present invention include Lac-regulatable, heat (hyperthermia)-inducible promoters, and radiation-inducible, for e.g., EGR [Joki et al., *Hum Gene Ther;* 6(12): 1507–13 (1995)], alpha-inhibin, RNA pol III tRNA met and other amino acid promoters. U1 snRNA [Bartlett et al., *Proc Nat'l Acad Sci USA,* 20;93(17): 8852–7 (1996)], MC-1, PGK, β-actin, and α-globin. Many other promoters that may be useful are listed in Walther and Stein [*J Mol Med* 74(7): 379–92 (1996)].

It is envisioned that any of the above promoters alone, or in combination with another, may be useful according to the present invention depending on the action desired. In addition, this list of promoters should not be construed to be exhaustive or limiting, and those of skill in the art will know of other promoters that may be used in conjunction with the promoters and methods disclosed herein.

Another regulatory element contemplated for use in the present invention is an enhancer. These are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization. Enhancers useful in the present invention are well known to those of skill in the art and will depend on the particular expression system being employed [Scharf et al., *Results Probl Cell Differ* 20: 125–62 (1994); Bittner et al., *Meth Enzymol* 153: 516–544 (1987)].

Polyadenylation Signals. Where a cDNA insert is employed, one will typically desire to include a polyadenylation signal to affect proper polyadenylation of the gene transcript. The nature of the polyadenylation signal is not believed to be crucial to the successful practice of the invention, and any such sequence may be employed, such as human or bovine growth hormone and SV40 polyadenylation signals. Also contemplated as an element of the expression cassette is a terminator. These elements can serve to enhance message levels and to minimize read-through from the cassette into other sequences.

IRES. In certain embodiments of the invention, the use of internal ribosome entry site (IRES) elements is contemplated to create multigene, or polycistronic, messages. IRES elements are able to bypass the ribosome scanning model of 5' methylated Cap dependent translation and begin translation at internal sites [Pelletier and Sonenberg, *Nature,* 334: 320–325 (1988)]. IRES elements from two members of the picornavirus family (poliovirus and encephalomyocarditis) have been described [Pelletier and Sonenberg (1988), supra], as well an IRES from a mammalian message [Macejak and Sarnow, *Nature,* 353: 90–94 (1991)]. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

b. Delivery of Expression Vectors.

There are a number of ways in which expression vectors may introduced into cells. In certain embodiments of the invention, the expression construct comprises a virus or engineered construct derived from a viral genome. In other embodiments, non-viral delivery is contemplated. The ability of certain viruses to enter cells via receptor-mediated endocytosis, to integrate into host cell genome and express viral genes stably and efficiently have made them attractive candidates for the transfer of foreign genes into mammalian cells [Ridgeway, In: Rodriguez R L, Denhardt D T, ed. Vectors: A survey of molecular cloning vectors and their uses. Stoneham: Butterworth, 467–492, 1988; Nicolas and Rubenstein, In: Vectors: A survey of molecular cloning vectors and their uses, Rodriguez & Denhardt (eds.), Stoneham: Butterworth, 493–513, 1988; Baichwal and Sugden, In: Gene Transfer, Kucherlapati R, ed., New York, Plenum Press, 117–148, 1986; Temin, In: gene Transfer, Kucherlapati (ed.), New York: Plenum Press, 149–188, 1986]. The first viruses used as gene vectors were DNA viruses including the papovaviruses (simian virus 40, bovine papilloma virus, and polyoma) [Ridgeway, (1988), supra; Baichwal and Sugden, (1986), supra] and adenoviruses [Ridgeway, (1988), supra; Baichwal and Sugden, (1986), supra]. These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals [Nicolas and Rubenstein, (1988), supra; Temin, (1986), supra].

It is now widely recognized that DNA may be introduced into a cell using a variety of viral vectors. In such embodiments, expression constructs comprising viral vectors containing the genes of interest may be adenoviral (see, for example, U.S. Pat. No. 5,824,544; U.S. Pat. No. 5,707,618; U.S. Pat. No. 5,693,509; U.S. Pat. No. 5,670,488; U.S. Pat. No. 5,585,362; each incorporated herein by reference), retroviral (see, for example, U.S. Pat. No. 5,888,502; U.S. Pat. No. 5,830,725; U.S. Pat. No. 5,770,414; U.S. Pat. No. 5,686,278; U.S. Pat. No. 4,861,719 each incorporated herein bad reference), adeno-associated viral (see, for example, U.S. Pat. No. 5,474,935; U.S. Pat. No. 5,139,941; U.S. Pat. No. 5,622,856; U.S. Pat. No. 5,658,776; U.S. Pat. No. 5,773,289; U.S. Pat. No. 5,789,390; U.S. Pat. No. 5,834,441; U.S. Pat. No. 5,863,541; U.S. Pat. No. 5,851,521; U.S. Pat. No. 5,252,479 each incorporated herein by reference), an adenoviral-adenoassociated viral hybrid (see, for example, U.S. Pat. No. 5,856,152 incorporated herein by reference) or a vaccinia viral or a herpesviral (see, for example, U.S. Pat. No. 5,879,934; U.S. Pat. No. 5,849,571; U.S. Pat. No. 5,830,727; U.S. Pat. No. 5,661,033; U.S. Pat. No. 5,328,688 each incorporated herein by reference) vector.

There are a number of alternatives to viral transfer of genetic constructs. This section provides a discussion of methods and compositions of non-viral gene transfer. DNA constructs of the present invention are generally delivered to a cell, and in certain situations, the nucleic acid or the protein to be transferred may be transferred using non-viral methods.

Several non-viral methods for the transfer of expression constructs into cultured mammalian cells are contemplated by the present invention. These include calcium phosphate precipitation [Graham and Van Der Eb, *Virology,* 52: 456–467 (1973); Chen and Okayama, *Mol Cell Biol,* 7: 2745–2752 (1987); Rippe et al., *Mol Cell Biol,* 10: 689–695 (1990)] DEAE-dextran [Gopal, *Mol Cell Biol,* 5: 1188–1190 (1985)], electroporation [Tur-Kaspa et al., *Mol Cell Biol,* 6: 716–718 (1986); Potter et al., *Proc Nat'l Acad Sci USA,* 81: 7161–7165 (1984)], direct microinjection [Harland and Weintraub, *J Cell Biol,* 101: 1094–1099 (1985)], DNA-loaded liposomes [Nicolau and Sene, *Biochim Biophys Acta,* 721: 185–190 (1982); Fraley et al., *Proc Nat'l Acad Sci USA,* 76: 3348–3352 (1979); Felgner, *Sci Amer* 276(6): 102–6 (1997); Feigner, *Hum Gene Ther* 7(15): 1791–3 (1996)], cell sonication [Fechheimer et al., *Proc Nat'l Acad Sci USA,* 84: 8463–8467 (1987)], gene bombardment using high velocity microprojectiles [Yang et al., *Proc Nat'l Acad Sci USA,* 87: 9568–9572 (1990)], and receptor-mediated transfection [Wu and Wu, *J Biol Chem,* 262: 4429–4432 (1987); Wu and Wu, *Biochemistry,* 27: 887–892 (1988); Wu and Wu, *Adv Drug Deliv Rev,* 12: 159–167 (1993)].

Once the construct has been delivered into the cell, the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell, and where in the cell the nucleic acid remains, is dependent on the type of expression construct employed.

In a particular embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers [Ghosh and Bachhawat, In: *Liver diseases, targeted diagnosis and therapy using specific receptors and ligands*, Wu G, Wu C ed., New York: Marcel Dekker, pp. 87–104, (1991)]. The addition of DNA to cationic liposomes causes a topological transition from liposomes to optically birefringent liquid-crystalline condensed globules [Radler et al., *Science,* 275(5301): 810–4 (1997)]. These DNA-lipid complexes are potential non-viral vectors for use in gene therapy and delivery.

Liposome-mediated nucleic acid delivery and expression of foreign DNA in vitro has been very successful. Also contemplated in the present invention are various commercial approaches involving "lipofection" technology. In certain embodiments of the invention, the liposome may be complexed with a hemagglutinating virus (HVJ). This has been shown to facilitate fusion with the cell membrane and promote cell entry of liposome-encapsulated DNA [Kaneda et al., *Science,* 243: 375–378 (1989)]. In other embodiments, the liposome maybe complexed or employed in conjunction with nuclear nonhistone chromosomal proteins (HMG-1) [Kato et al., *J Biol Chem,* 266: 3361–3364 (1991)]. In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other vector delivery systems that can be employed to deliver a nucleic acid encoding a therapeutic gene into cells include receptor-mediated delivery vehicles. These take advantage of the selective uptake of macromolecules by receptor-mediated endocytosis in almost all eukaryotic cells. Because of the cell type-specific distribution of various receptors, the delivery can be highly specific [Wu and Wu, (1993), supra].

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) [Wu and Wu, (1987), supra] and transferrin [Wagner et al., *Proc Nat'l*

*Acad Sci USA,* 87(9): 3410–3414 (1990)]. Recently, a synthetic neoglycoprotein, which recognizes the same receptor as ASOR, has been used as a gene delivery vehicle [Ferkol et al., *FASEB J.* 7: 1081–1091 (1993); Perales et al., *Proc Nat'l Acad Sci USA,* 91: 4086–4090 (1994)] and epidermal growth factor (EGF) has also been used to deliver genes to squamous carcinoma cells (Myers, EPO 0273085).

In other embodiments, the delivery vehicle may comprise a ligand and a liposome. For example, Nicolau et al. [*Meth Enzymol,* 149: 157–176 (1987)] employed lactosyl-ceramide, a galactose-terminal asialganglioside, incorporated into liposomes and observed an increase in the uptake of the insulin gene by hepatocytes. Thus, it is feasible that a nucleic, acid encoding a therapeutic gene also may be specifically delivered into a particular cell type by any number of receptor-ligand systems with or without liposomes.

In another embodiment of the invention, the expression construct may simply consist of naked recombinant DNA or plasmids. Transfer of the construct may be preformed by any of the methods mentioned above that physically or chemically permeabilize the cell membrane. This is applicable particularly for transfer in vitro, however, it may be applied for in vivo use as well. Dubensky et al. [*Proc Nat'l Acad Sci USA,* 81: 7529–7533 (1984)] successfully injected polyomavirus DNA in the form of $CaPO_4$ precipitates into liver and spleen of adult and newborn mice demonstrating active viral replication and acute infection. Benvenisty and Neshif [*Proc Nat'l Acad Sci USA,* 83:9551–9555 (1986)] also demonstrated that direct intraperitoneal injection of $CaPO_4$ precipitated plasmids results in expression of the transfected genes.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them [Klein et al., *Nature,* 327: 70–73 (1987)]. Several devices for accelerating small particles have been developed. One such device relies on a high voltage discharge to generate an electrical current, which in turn provides the motive force [Yang et al., *Proc Nat'l Acad Sci USA,* 87: 9568–9572 (1990)]. The microprojectiles used have consisted of biologically inert substances such as tungsten or gold beads.

F. Methods of Treating Hemophilia B.

As mentioned herein above, it is contemplated that the mutant human factor IX protein or the vectors comprising a polynucleotide encoding such a protein will be employed in replacement therapy protocols for the treatment of hemophilia B.

a. Protein Based Therapy

One of the therapeutic embodiments of the present invention is the provision, to a subject in need thereof, compositions comprising the mutant human factor IX protein of the present invention. As discussed above, the protein may have been generated through recombinant means or by automated peptide synthesis. The factor IX formulations for such a therapy may be selected based on the route of administration and may include liposomal formulations as well as classic pharmaceutical preparations.

The mutant human factor IX proteins are formulated into appropriate preparation and administered to one or more sites within the subject in a therapeutically effective amount. In particularly preferred embodiments, the mutant human factor IX protein based therapy is effected via continuous or intermittent intravenous administration. By "therapeutically effective amount" the present invention refers to that amount of mutant human factor IX that is sufficient to produce or enhance the coagulation of blood in a mammal following a bleed. For example, a therapeutically effective amount may enhance coagulation by reducing clotting times in a blood coagulation assay, or even increase formation of intrinsic tenase or factor X activation. Blood coagulation assays are well known to those of skill in the art and are described for example, in Walter et al., [*Proc Nat'l Acad Sci USA,* 93: 3056–3061 (1996); Hathaway and Goodnight (1993), Laboratory Measurement of Hemostasis and Thrombosis, In: Disorders of Hemostasis and Thrombosis: A Clinical Guide, pp. 21–29)].

Those of skill in the art will understand that the amounts of mutant human factor IX for therapeutic use may vary. It is contemplated that the specific activity of the factor IX protein preparation may be in the range of from about 100 units/mg of protein to about 500 units/mg protein. Thus, a given preparation of mutant human factor IX may comprises about 100 units/mg protein, about 125 units/mg protein, about 150 units/mg protein, about 175 units/mg protein, about 200 units/mg protein, about 225 units/mg protein, about 250 units/mg protein, about 275 units/mg protein, about 300 units/mg protein, about 325 units/mg protein, about 350 units/mg protein, about 375 units/mg protein, about 400 units,/mg protein, about 425 units/mg protein, about 450 units/mg protein, about 475 units/mg protein and about 500 units/mg protein. A particularly preferred range is from about 100 units/mg protein to about 200 units/mg protein, a more preferable range is between about 150 to about 200 units/mg protein. Preferably, the protein composition is substantially free of contaminating factor IXa and has a factor IXa contamination level of less than 0.02% (w/w). Factor IX compositions, suitable for injection into a patient, can be prepared for example, by reconstitution with a pharmacologically acceptable diluent of a lyophilized sample comprising purified factor IX and stabilizing salts.

Administration of the compositions can be systemic or local and may comprise a single-site injection of a therapeutically effective amount of the mutant human factor IX protein composition. Any route known to those of skill in the art for the administration of a therapeutic composition of the invention is contemplated including for example, intravenous, intramuscular, subcutaneous, or a catheter for long-term administration. Alternatively, it is contemplated that the therapeutic composition may be delivered to the patient at multiple sites. The multiple administrations may be rendered simultaneously or may be administered over a period of several hours. In certain cases it may be beneficial to provide a continuous flow of the therapeutic composition. Additional therapy may be administered on a periodic basis, for example, daily, weekly, or monthly.

b. Genetic Based Therapies.

Another therapeutic embodiment contemplated by the present invention is a method of treating a mammal having hemophilia comprising administering to the mammal a gene therapy based pharmaceutical composition. Specifically, the present inventors intend to provide, to a given tissue in a patient or subject in need thereof, an expression construct capable of providing the mutant human factor IX to that patient in a functional form. It is specifically contemplated that a gene encoding the mutant human factor IX will be employed in human therapy. The lengthy discussion of expression vectors and the genetic elements employed therein is incorporated into this section by reference. Particularly preferred expression vectors are viral vectors such as adenovirus, adeno-associated virus, herpesvirus, vaccinia virus, and retrovirus. Also preferred is a liposomally-encapsulated expression vector.

Those of skill in the art are well aware of how to apply gene delivery in vivo. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Various routes are contemplated for delivery. The section below on routes contains an extensive list of possible routes. For example, systemic delivery is contemplated. In other cases, a variety of direct, local and regional approaches may be taken. For example, where the individual being treated exhibits a localized bleed, that area may be directly injected with the expression vector.

In certain embodiments, it is contemplated that a preparation of the vector comprising the mutant human factor IX encoding polynucleotide is injected into the muscle tissue of an animal at a single site per dose. In other embodiments, the preparation is injected into the muscle tissue of the animal either simultaneously, or over the course of several hours, at multiple muscle tissue sites. In the latter instance, when the method comprises simultaneous multiple injections of viral vector genomes, it is envisaged that a multiple delivery injection device may be used such that different areas of muscle tissue receive the vector simultaneously.

Incorporated herein by reference is U.S. Pat. No. 6,093,392 that describes methods of gene therapy for hemophilia, which employ adeno-associated viral vectors. Similarly, U.S. Pat. No. 5,935,935 is incorporated herein by reference and describes the use of adenoviral vectors for the treatment of hemophilia. It is contemplated that the methods described therein will be useful in combination with the compositions of the present invention.

Also incorporated herein by reference is U.S. Pat. No. 5,681,746, which describes retroviral vectors for the expression of factor VIII and pharmaceutical compositions and methods of using such vectors for treating hemophilia. The present invention contemplates gene therapy protocols in which such retroviral particles comprising mutant human factor IX compositions of the present invention may be used for the treatment of mammals afflicted with hemophilia c. Combination Therapy In addition to therapies based solely on the delivery of the mutant human factor IX, combination therapy is specifically contemplated. In the context of the present invention, it is contemplated that the mutant human factor IX therapy could be used similarly in conjunction with other agents for commonly used for the treatment of hemophilia.

To achieve the appropriate therapeutic outcome, using the methods and compositions of the present invention, one would generally provide a composition comprising the mutant human factor IX and at least one other therapeutic agent (second therapeutic agent). In the present invention, it is contemplated that the second therapeutic agent may be one or more other factors involved in the blood coagulation cascade. For example, it is contemplated that the compositions comprising the mutant human factor IX of the present invention may be combined with activated prothrombin complex concentrates, factors II, VII, VIIa, VIII, X, precursor Xa, protein C, XI and XII.

The combination therapy compositions would be provided in a combined amount effective to produce the desired therapeutic outcome of blood coagulation. This process may in-solve contacting the cells with the mutant human factor IX and the second agent(s) or factor(s) at the same time. This may be achieved by administering a single composition or pharmacological formulation that includes both agents, or by administering two distinct compositions or formulations, at the same time, wherein one composition includes the mutant human factor IX therapeutic composition and the other includes the second therapeutic agent.

Alternatively, the mutant human factor IX treatment may precede or follow the other agent treatment by intervals ranging from minutes to weeks. In embodiments where the second therapeutic agent and the mutant human factor IX are administered separately, one would generally ensure that a significant period of time did not expire between the time of each delivery, such that the second agent and mutant human factor IX would still be able to exert an advantageously combined effect. In such instances, it is contemplated that one would administer both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Local delivery of mutant human factor IX expression constructs or proteins to patients may be a very efficient method for delivering a therapeutically effective gene to counteract the immediate clinical manifestations of the disease, i.e., localized bleeding. Similarly, the second therapeutic agent may be directed to a particular, affected regions of the subject's body. Alternatively, systemic delivery of the mutant human factor IX and/or the second therapeutic agent may be appropriate in certain circumstances.

G. Assays for Factor IX Activity

In certain aspects of the present invention, it may be necessary to determine the activity of mutant human factor A. In particular, the effect of the therapeutic compositions of the present invention on blood coagulation activity may need to be monitored Those of skill in the art are aware of numerous blood coagulation assays some of which are described in the present section. This is by no means intended to be an exhaustive list of such assays and is merely intended to provide certain exemplary assays well known to those of skill in the art that may be used in determining the blood coagulation activity of the present invention. Further, the present section also describes assays for the determination of heparin inhibition of factor IX activity. Exemplary in vitro and in vivo assays for determining these activities are provided herein below.

a. In Vitro Assays

A chromogenic in vitro assay may be used to determine the human factor IX activity of a given mutant human factor IX of the present invention. Factor IXa has poor reactivity toward chromogenic substrates, likely due to the partially collapsed nature of the active site [Brandstetter et al., *Proc Nat'l Acad Sci USA,* 92(21): 9796–800 (1995)]. However, the addition of 30% ethylene glycol can increase the catalytic rate nearly ten fold, especially for substrates with hydrophobic moieties in the P3 position [Sturzebecher et al., *FEBS Letters,* 412(2): 295–300 (1997)]. The effect of mutations in the heparin binding site of factor IXa on cleavage of the chromogenic substrates, Pefachrome IXa ($CH_3SO_2$-D-

CHG-Gly-Arg-pNA) or CBS 31.39 ($CH_3SO_2$DLeu-Gly-Arg-p-nitroanilide), can be assessed by incubating increasing amounts of heparin with 25 nM enzyme in 0.15 M NaCl, 2 mM $CaCl_2$, 20 mM HEPES, pH 7.4, 30% ethylene glycol and 2.5 mM Pefachrome IXa or 4 mM CBS 31.39 in a microtiter plate. Initial rates are determined by the change in absorbance at 405 nm over 5–10 min a Vmax Reader. The $K_m$ of CBS 31.39 for factor IXa is 3.7 mM under these conditions.

An in vitro assay for intrinsic complex activity to determine factor IX activity also may be used. In this assay, thrombin-activated factor VIIIa (final concentration 0.5 nM) is added to a reaction containing 5 nM factor IXa, 5% (v/v) rabbit brain cephalin, 300 nM factor X, and increasing concentrations of heparin in 0.15 M NaCl, 20 mM HEPES, pH 7.4, 2 mM CaCl2, and 0.1% PEG-8000. The reaction are sampled (50 μl) at 15, 30, 45, and 60 sec into 10 μl of 0.25 M EDTA, pH 8.0. The chromogenic substrate S-2765 is then added at 300 μM and the amount of factor Xa generated determined by comparison of the rate of cleavage with a standard curve. The assay for intrinsic tenase activity may be modified to be performed in the presence of excess factor VIIIa (5 nM) and the linear range for factor IXa determined (as previously described for factor VIIIa) for accurate quantitation of the mutant activities. Significant differences in catalytic activity may be further analyzed by determination of the Km and kcat for factor X activation by intrinsic tenase for wild-type and mutant factor IXa. The affinity of mutant factor IXa-factor VIIIa complex formation in the presence of phospholipid can be compared to wild-type factor IXa in a kinetic binding assay.

The relative affinity of heparin for the mutant human factor IXa proteins can be determined by titration of active site-labeled protease. The interaction of heparin with F1-EGR-factor IXa can be detected by the change in emission fluorescence intensity at 525 nm. To generate the active site-labeled proteases, wild-type and mutant human factor IX is activated by incubation with factor XIa. Conditions for complete activation can be confirmed by SDS-PAGE for each mutant protein. The mutant factor IXa is then incubated with ten-fold molar excess of fluorescein-EGR-chloromethylketone (Hematologic Technologies) for 30 min at 23° C., followed by gel filtration chromatography on a G-100 column (fractionation range 4–100 kDa) to separate factor XIa (void volume) and the low molecular weight free inhibitor from F1-EGR-factor IXa. The sample may then be subjected to additional dialysis if necessary to completely remove free inhibitor. Labeled proteases will then be quantitated by $A_{280}$. The F1-EGR-factor IXa (25 nM) is titrated with size-fractionated heparin chains to generate binding curves. The binding curves for mutant factor IXa can be compared to wild-type under identical conditions, with fitting to an appropriate site-specific binding model to provide a KD(obs) [Olson et al., *J Biol Chem,* 266(10): 6342–52 (1991)]. An estimate of the relative affinity of mutant human factor IXa for heparin (i.e. rank order) is sufficient to correlate with the relative effect of mutations on enzymatic activity and inhibition by heparin. This strategy is similar to that used to map the heparin binding site of thrombin, where NaCl elution from heparin-sepharose was used as an estimate of heparin affinity, allowing correlation of elution position with the rate constant for inhibition by ATIII-heparin [Sheehan and Sadler, *Proc Nat'l Acad Sci USA,* 91(12): 5518–22 (1994)].

In vitro blood coagulation assays also are well known to those of skill in the art and are described, for example, in Walter et al., [*Proc Nat'l Acad Sci USA,* 93: 3056–3061 (1996); Hathaway and Goodnight (1993), Laboratory Measurement of Hemostasis and Thrombosis, In: Disorders of Hemostasis and Thrombosis: A Clinical Guide, pp. 21–29)]. These assays may be used in the present invention to ensure that the mutant human factor IX possesses an appropriate blood coagulation effect. Those of skill in the art also are referred to "A Laboratory Manual of *Blood* Coagulation" Austen et al., Blackwell Scientific Publishing (1975) for additional methods for conducting blood clotting assays.

In preferred embodiments, the effect of mutations in the heparin binding exosite on the coagulant activity of mutant human factor IX is assessed by performing an activated partial thromboplastin time (APTT) in factor IX deficient plasma [Bajaj et al, *Meth Enzymol,* 222: 96–128 (1993)]. The relative coagulant activity of the mutants is determined by comparison to a standard curve. The APTT reflects both activation of the mutant human factor IX by factor XIa, and the enzymatic activity of the protease in plasma. Unexpected differences can be further analyzed by comparing mutant human factor IX and factor IXa plasma coagulant activity of the mutants to wild-type, in order to differentiate effects on activation versus enzymatic activity.

b. In Vivo Assays

Before the mutant human factor IX compositions of the present invention are employed in human therapeutic protocols, it may be desirable to monitor the effects of such compositions in animal models. There are a number of animal models, in vivo assays, previously described by those of skill in the art that may be useful in the present invention.

An exemplary animal model for hemophilia B is available. For example, a colony of mice having severe hemophilia B are well known to those of skill in the art [Lin et al., *Blood,* 90(10): 3962–6 (1997); Kung et al., *Blood,* 91(3): 784–90 (1998); Snyder et al., *Nat Med,* 5(1): 64–70 (1999)]. Additionally, a colony of dogs having severe hemophilia B comprising males that are hemizygous and females that are homozygous for a point mutation in the catalytic domain of the canine factor IX gene, have been maintained for more than two decades at the University of North Carolina, Chapel Hill [Evans et al., *Blood* 74: 207–212 (1989)].

The hemostatic parameters of the above mice and dogs are well described. For example, in the dogs there is an absence of plasma factor IX antigen, whole blood clotting times of>60 minutes, whereas normal dogs are 6–8 minutes, and prolonged activated partial thromboplastin time of 50–80 seconds, whereas normal dogs are 13–18 seconds. These dogs experience recurrent spontaneous hemorrhages. Typically, significant bleeding episodes are successfully managed by the single intravenous infusion of 10 mL/kg of normal canine plasma; occasionally, repeat infusions are required to control bleeding.

In order to determine the efficacy of the mutant human factor IX protein and gene therapy compositions of the present invention, such mice and dogs may be injected intramuscularly and/or intravenously with the compositions of the present invention and the blood clotting time in the presence and absence of the compositions may be determined. Such determinations will be helpful in providing guidance on the dosages and times of administration and the efficacy of a given composition against hemophilia B. In gene therapy protocols, immunofluorescence staining of sections obtained from biopsied muscle may be performed, and expression of the mutant human factor IX in the transduced muscle fibers may be determined.

H. Pharmaceutical Compositions

In order to prepare mutant human factor IX containing compositions for clinical use, it will be necessary to prepare the viral expression vectors, proteins, and nucleic acids as pharmaceutical compositions, i.e., in a form appropriate for in vivo applications. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the mutant human factor IX or an expression vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents dispersion media, coatings, antibacterial and antifungal agents, isotonic and absorption delaying agents, and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention include classic pharmaceutical preparations. Administration of these compositions according to the present invention will be via any common route so long as the target tissue is available via that route. The pharmaceutical compositions may be introduced into the subject by any conventional method, e.g., by intravenous, intradermal, intramusclar, intramammary, intraperitoneal, intrathecal, retrobulbar, intrapulmonary (e.g. term release); by oral, sublingual, nasal, anal, vaginal, or transdermal delivery, or by surgical implantation at a particular site. The treatment may consist of a single dose or a plurality of doses over a period of time.

The active compounds may be prepared for administration as solutions of free base or pharmacologically acceptable salts in water, suitably mixed with a surfactant, such as hydroxypropylcellulose. Dispersions also can be prepared in glycerol, liquid polyethylene glycols, and mixtures thereof, and in oils. Under ordinary conditions of storage and use, these preparations contain a preservative to prevent the growth of microorganisms.

The pharmaceutical forms, suitable for injectable use, include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum-drying and freeze-drying techniques that yield a powder of the active ingredient plus any additional desired ingredient from a previously sterile-filtered solution thereof As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms, such as injectable solutions, drug release capsules and the like. For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous and intraperitoneal administration.

"Unit dose" is defined as a discrete amount of a therapeutic composition dispersed in a suitable carrier. For example, where polypeptides are being administered parenterally, the polypeptide compositions are generally injected in doses ranging from 1 μg/kg to 100 mg/kg body weight/day, preferably at doses ranging from 0.1 mg/kg to about 50 mg/kg body weight/day. In terms of units of mutant human factor IX activity per kg of weight of subject, it is contemplated that between about 100 to about 500 units/kg body weight will be useful. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See, for example, Remington's Pharmaceutical Sciences, 18th Ed. (1990), Mack Publ. Co, Easton Pa. 18042, pp. 1435–1712, incorporated herein by reference. Such formulations may influence the physical state, stability, rate of in vivo release and rate of in vivo clearance of the administered agents. Depending on the route of administration, a suitable dose may be calculated according to body weight, body surface area, or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

Appropriate dosages may be ascertained through the use of established assays for determining blood clotting levels in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration, and other clinical factors. As studies are conducted, further information will emerge regarding appropriate dosage levels and duration of treatment for specific diseases and conditions.

In gene therapy embodiments employing viral delivery, the unit dose may be calculated in terms of the dose of viral particles being administered. Viral doses include a particular number of virus particles or plaque forming units (pfu). For embodiments involving adenovirus, particular unit doses include $10^3$, $10^4$, $10^5$, $10^6$, $10^7$, $10^8$, $10^9$, $10^{10}$, $10^{11}$, $10^{12}$, $10^{13}$ or $10^{14}$ pfu. Particle doses may be somewhat higher (10 to 100-fold) due to the presence of infection defective particles.

It will be appreciated that the pharmaceutical compositions and treatment methods of the invention may be useful in fields of human medicine and veterinary medicine. Thus, the subject to be treated may be a mammal, preferably human or other animal. For veterinary purposes, subjects include, for example, farm animals including cows, sheep, pigs, horses and goats, companion animals, such as dogs and cats, exotic and/or zoo animals, laboratory animals including mice rats, rabbits, guinea pigs and hamsters, and poultry such as chickens, turkeys, ducks, and geese.

I. Examples

The present invention is described in more detail with reference to the following non-limiting examples, which represent preferred embodiments of the invention. Those of skill in the art will understand that the techniques described in these examples represent techniques described by the inventors to function well in the practice of the invention, and as such constitute preferred modes for the practice thereof. However, it should be appreciated that those of skill in the art should in light of the present disclosure, appreciate that many changes can be made in the specific methods that are disclosed and still obtain a like or similar result without departing from the spirit and scope of the invention.

EXAMPLE 1

Transient Expression of Human Factor IX

Construction and Transient Expression of Factor IX Constructs. The recombinant human factor IX cDNA in the expression vector pCMV5 was generously provided by Darrel Stafford (Univ. North Carolina). The EcoRI fragment of the cDNA insert was excised from the pCMW5-human factor DC expression vector and subcloned into pBluescript SK II for mutagenesis. Mutations are constructed by PCR using a high fidelity DNA polymerase (pfu) followed by Dpn I digestion of the parental plasmid (QuikChange Mutagenesis Kit, Strategene). Following transformation, clones containing the desired mutation(s) are selected by DNA sequencing. The EcoRI fragment is excised from plasmids with the desired mutation(s) and subcloned back into the pCMV5 expression vector. Proper orientation of the constructs for expression is confirmed by restriction digest with Bam HI/Bgl II. Mutant factor IX cDNA constructs are screened for protein expression and initial characterization as described below.

Initial Characterization of Transiently Expressed Factor IX Proteins. The use of initial characterization of constructs in transient transfections will allow one of skill in the art to monitor and modify the results of the mutagenesis strategy to assist in the selection of stable cell lines and purification of the mutant protein.

The pCMV5-HuFIX wild-type construct was transiently transfected into 293 cells with Lipofectin (Gibco-BRL). Following transfection, cells were incubated in serum free media (SFM) containing 10 μg/mL Vitamin K for 48 hr. The SFM was harvested, concentrated 10–12 fold by Centricon-30, and assayed for clotting and intrinsic tenase activity.

Clotting activity and intrinsic tenase activity were easily detected in the media, with no significant background detected with mock-transfected cells. Factor IX antigen concentration was determined using a "sandwich" type ELISA with affinity purified sheep anti-human factor IX polyclonal antibody (Hematologic Technologies) as the capture antibody, and a horseradish peroxidase-conjugated affinity purified sheep anti-human factor IX antibody (Enzyme Research) to detect the immobilized antigen. The assay demonstrated a linear relationship (log-log plots) from 0.1 to 100 μg/mL human factor IX, and estimated factor IX concentrations in the 0.6 μg/mL range (10–12 nM) following transient transfection of pCMV5-factor IX.

Factor X activation by the mutant proteins may be determined in the intrinsic tenase assay following activation from the zymogen form with factor XIa. In this method, thrombin-activated factor VIIIa (final concentration 0.5 nM) is added to a reaction containing 5 nM factor IXa, 5% (v/v) rabbit brain cephalin, 300 nM factor X, and increasing concentrations of heparin in 0.15 M NaCl, 20 mM HEPES, pH 7.4, 2 mM $CaCl_2$, and 0.1% PEG-8000. The reaction is sampled (50 μl) at 15, 30, 45, and 60 sec into 10 μl of 0.25 M EDTA, pH 8.0. The chromogenic substrate, S-2765, is then added at 300 μM and the amount of factor Xa generated determined by comparison of the rate of cleavage with a standard curve [Sheehan and Lan, *Blood,* 92(5): 1617–1625 (1998)]. Alternatively, this chromogenic assay for factor Xa generation can be made more quantitative for factor IXa (0.5 nM) by performing it in the presence of excess factor VIIIa (5 nM).

Coagulant activity of the mutant proteins is determined by an APTT in factor IX deficient plasma, with comparison to a standard curve [Bajaj et al., *Meth Enzymol,* 222: 96–128 (1993)].

EXAMPLE 2

Stable Expression and Purification of Human Factor IX

The present example provides methods for the recombinant expression and purification of recombinant human factor IX. Stable cell lines expressing recombinant factor IX are selected for large scale production of protein, and factor IX is purified to homogeneity from serum-free conditioned media.

Stable cell lines expressing recombinant human factor IX were obtained by co-transfecting ScaI-linearized pCMV5-huFIX and pSV2neo plasmids into 293 cells by the calcium phosphate method, and selecting clones by limiting dilution in G418. Cell lines expressing high levels of the recombinant factor IX were determined by ELISA and/or Western blot. Cell lines with the highest expression levels were then expanded for large-scale culture in T-225 $cm^2$ flasks. Upon reaching confluence, the growth media (50% DME/50% F-12/10% FCS) was removed, the monolayers washed extensively with SFM, and replaced with SFM supplemented with insulin-transferrin-sodium selenite (Sigma) and 10 μg/mL vitamin K. Conditioned media was collected every 48 hours for 10 days. Benzamidine was added to a final concentration of 5 mM, and the conditioned media frozen at −20° C. to −25° C. Upon thawing, the conditioned media was pooled, filtered, and subjected to barium chloride precipitation [Cote et al., *J Biol Chem,* 269(15):11374–80 (1994)]. The precipitate was dissolved in 0.2 M EDTA, and the eluate dialyzed overnight before application to a Mono Q HR 5/5 column (0.15 M NaCl, 20 mM HEPES, pH 7.4, 0.1% PEG-8000). Human factor IX was eluted with a calcium chloride gradient (0–45 mM) and concentrated in a Centricon-30.

Figure 1:
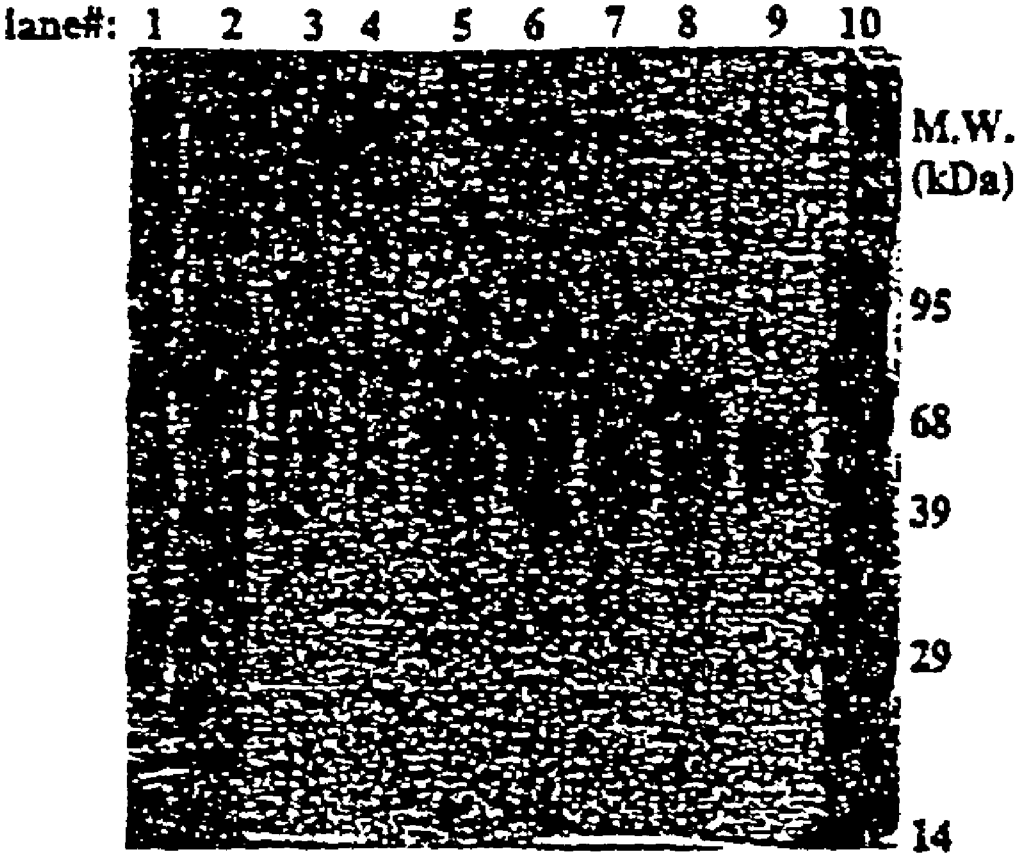
FIG. 1. Purification of recombinant human factor IXa from 293 cells. Sliver stained nonreducing 10% SDS-PAGE representing samples from purification steps. Lane 1 and 10-molecular weight markers, lane 2- conditioned media, lane 3 barium depleted media, lane 4-barium eluate, lane 5–9 fractions 17, 18, 19, 20, and 23 eluted from Mono Q HR 5/5 with calcium chloride gradient (0–30 mM). The human factor IX isolated using this method demonstrated high purity by 10% SDS-PAGE with silver staining, high specific clotting activity (187 U/mg), and an overall yield of approximately 30% by ELISA.

Purity of factor IX proteins was assessed by SDS-PAGE with silver staining, and the factor IX concentration was determined by A280 (1%=13.3) and ELISA. The human factor IX isolated above demonstrated high purity by 10% SDS-PAGE with silver staining (FIG. 1), high specific clotting activity (187 U/mg), and an overall yield of approximately 30% by ELISA. Additionally, elimination of factor IX antigen with low clotting activity (partial degradation or incomplete carboxylation) was detected by Western blot following 2 M NaCl elution of the Mono Q column following the calcium chloride gradient.

Other studies maybe used to determine the activity of the recombinant factor IXa. Recombinant factor IX may be activated by incubation with human factor XIa (Enzyme Research) at a molar ratio of 100:1 in 150 mM NaCl, 20 mM HEPES, 2 mM CaCl2, pH 7.4. for 2 hr at 37° C. Activation is monitored by SDS-PAGE, and factor IXa specific activity estimated by active site titration with antithrombin [Chang et al., *J Biol Chem,* 273(20): 12089–94 (1998)].

Using the methods described in the present example, it is possible to purify highly active recombinant factor IX to homogeneity for detailed analysis of enzymatic and binding properties.

EXAMPLE 3

Three-Dimensional Model of Factor IX

A three-dimensional structure of human factor IXa was obtained by homology modeling with SWISS-MODEL, using the crystal structures of recombinant human factor IXa complexed with p-aminobenzamidine (1RFN), porcine factor IXa complexed with D-FPR-chloromethylketone (1PFX), human factor VIIa with soluble tissue factor (1DAN), and human factor Xa complexed with the synthetic inhibitor FX-2212A (1XKA, 1XKB) as templates [Hopfner et al., *Structure Fold Des,* 7(8): 989–96 (1999); Brandstetter et al., *Proc Nat'l Acad Sci USA,* 92(21): 9796–800 (1995); Banner et al., *Nature,* 380(6569): 41–6 (1996)]. The availability of a three-dimensional model of the protease is extremely helpful for planning and modification of the mutagenesis strategy.

EXAMPLE 4

Expression of Mutant Human Factor IX

The factor IX R233A construct was transiently expressed in 293 cells, concentrated by Centricon-30, and tested for clotting and intrinsic tenase activity. Initial experiments demonstrated roughly equivalent clotting activity to wild-type factor IX in factor IX-deficient plasma. After activation with factor XIa in conditioned media, the inhibitory effects of heparin on intrinsic tenase activity were tested in the presence of excess factor VIIIa. The relationship between clotting activity and intrinsic tenase activity in the absence of inhibitors was roughly proportionate for both recombinant proteases. Compared to wild-type factor IXa, the mutant R233A demonstrated markedly reduced inhibition by heparin.

Figure 2:
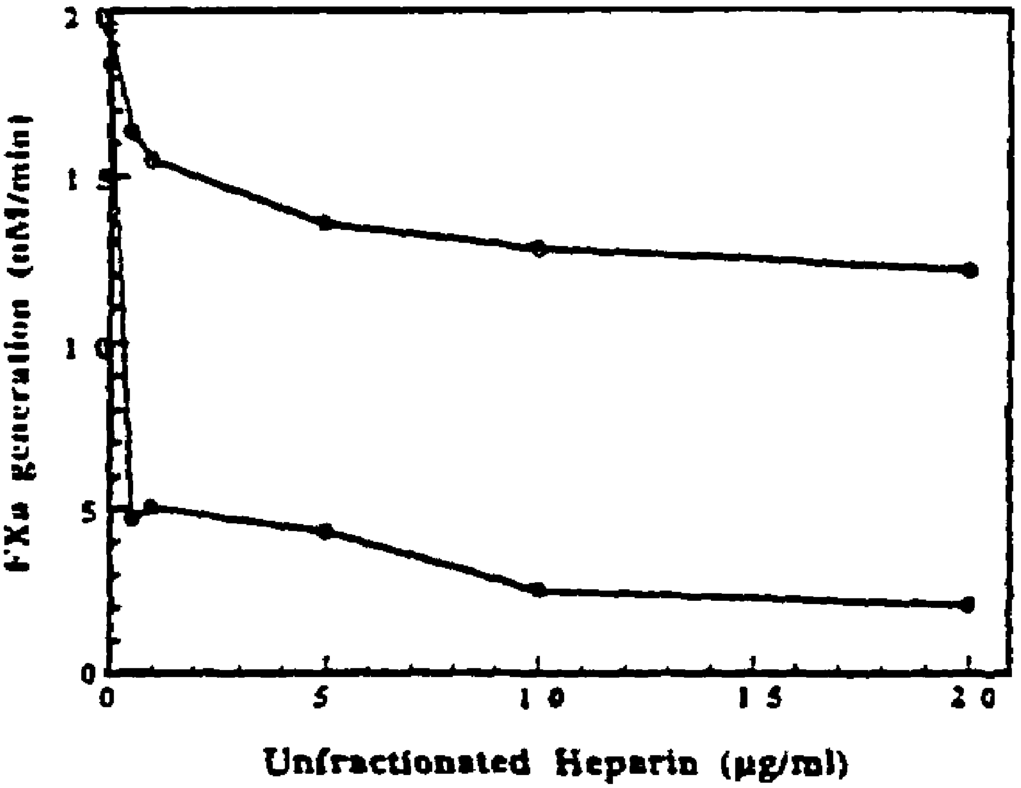
FIG. 2. Effect of unfractionated heparin on intrinsic tenase activity using recombinant factor IXa in conditioned media. Serum-free media incubated for 48 hr following transient transfection of 293 cells was concentrated by Centricon-30 and activated with 2 nM human factor XIa for 2 hr at 37° C. The intrinsic tenase assay was performed in which factor Via was in excess (5 nM), and conditioned media served as the enzyme source. The rate of factor Xa generation in the presence of increasing amounts of unfractionated heparin is plotted for wild-type (●) and R233A (○) factor IXa. Mock-transfected media demonstrated no significant activity. There was an increase in the residual activity in the plateau phase for the mutant R233A (~65%) relative to wild-type factor IXa (~15%).

Although a KJ cannot be calculated from the transient transfection data, a marked increase in the residual activity in the plateau phase was noted for the mutant R233A (~65%) relative to wild-type factor IXa (~15%) (FIG. 2). Similar effects on heparin inhibition were noted in transient transfection experiments with the factor IX K241A construct.

EXAMPLE 5

Comparison of In Vitro Antithrombin-Independent Inhibition of Wild-Type and Mutant R-233A Human Factor IXa by Unfractionated Heparin The present example demonstrates the resistance of the purified factor IXa mutant R233A to antithrombin independent inhibition by unfractionated heparin. Factor Xa generation by 5 nM wild-type (●) or R233A (○) factor IXa in the intrinsic tenase complex (0.5 nM factor VIIIa. 5% rabbit brain cephalin, 300 nM factor X and 2 mM $CaCl_2$) was determined in the presence of increasing amounts of unfractionated heparin (as described in Example 1; also, see FIG. 4). The data were fit by nonlinear regression to the equation for partial, uncompetitive inhibition. The mutant factor IXa R233A demonstrates increased resistance to inhibition by heparin, as demonstrated by the significant reduction in maximal inhibition (increase in enzymatic activity) observed relative to wild-type factor IXa.

EXAMPLE 6

Kinetic Analysis of Activation by Human Factor XIa on Wild-Type and Recombinant Human Factor IXa Mutant Proteins 293 cells were co-transfected with pSV2neo and pCMV5-huFIX constructs, and stable cell-lines expressing the recombinant human factor IX proteins were selected by resistance to the antibiotic G418. Human factor A. H92A, R233A, and K241A were purified to homogeneity from conditioned media. Clotting activity was determined in an APTT assay performed in factor IX deficient plasma (Table D). Wild-type and factor IX R233A were activated to factor IXa with human factor XIa. Analysis of the time course for factor IX activation by human factor XIa on an 10% SDS-PAGE gel demonstrated no significant difference between wild-type factor IX and the mutant R233A.

Figure 4A:
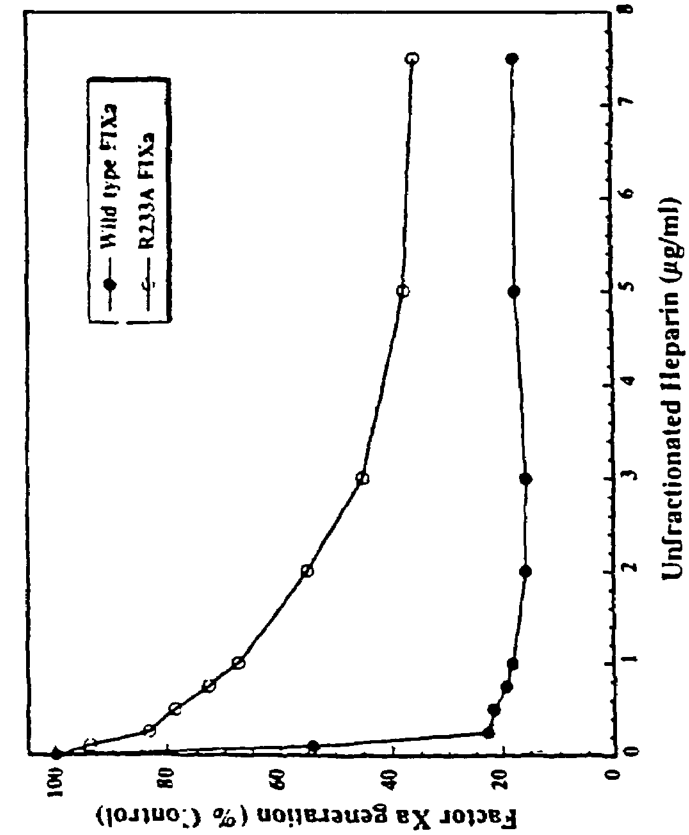
FIG. 4A and FIG. 4B. The rate of factor Xa generation by 5 nM wild-type (●) or R233A (○) factor IXa in the factor IXa-phospholipid (A) and the intrinsic tenase (B) complexes in the presence of increasing amounts of unfractionated heparin. Tie mutant factor Ma R233A demonstrates increased resistance to inhibition by heparin relative to wild-type factor IXa.
Figure 4B:
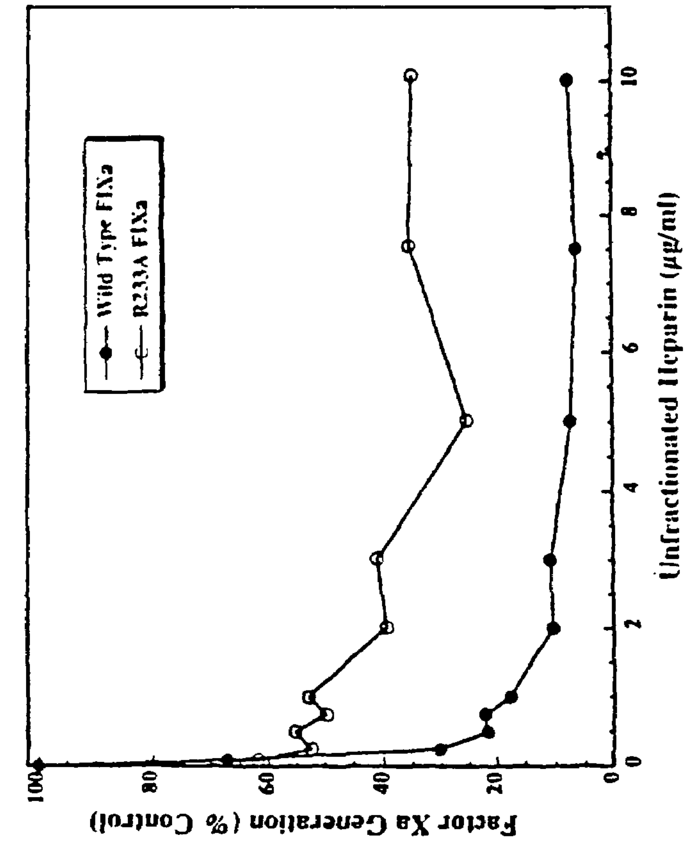

Following activation to factor IXa, the ability of heparin to inhibit factor X activation by the recombinant proteins was examined for both the factor IXa-phospholipid (in the presence of 30% ethylene glycol) and intrinsic tenase complex (factor VIIIa-factor IXa-phospholipid) (FIGS. 4A and 4B). Factor IXa R233A demonstrated resistance to inhibition by heparin relative to wild-type factor IXa under both assay conditions, suggesting that this mutation adversely affected the interaction of factor IXa with heparin.

TABLE D

Relative Heparin Affinity and Clotting Activity of Recombinant Factor IX Mutant Proteins.

| Protein | Heparin-Sepharose Elution (M NaCl) | Clotting Activity (% normal) |
|---|---|---|
| Plasma-derived factor IX | 0.49 | N.D. |
| Plasma-derived factor IXa | 0.58 | 100% |
| Wild-type factor IXa | 0.58 | 90% |
| Factor IXa H92A | 0.54 | 93% |
| Factor IXa R170A | 0.56 | N.D. |
| Factor IXa R233A | 0.33 | 36% |
| Factor IXa K241A | 0.56 | 55% |

Relative heparin affinity was determined in purified plasma-derived or recombinant factor IX. Control or mutant protein (30 μg) wasactivated with 25 nM human factor XIa (200:1, substrate:enzyme) for 2 hr at 37° C. and then applied to a heparin-sepharose column(1 mL) at a flow rate of 0.5 mL/min. The column was washed with 10 mL of 0.05 M NaCl, 20 mM HEPES, pH 7.4, 0.1% PEG-8000, and 5 mM EDTA,followed by elution with a 0.05 to 1.0 M NaCl gradient at 1 mL/min. Clotting activity was determined in an APTT assay performed byaddition of the zymogen from (factor IX) to factor IX deficient plasma (with comparison to a standard curve).

EXAMPLE 7

Heparin Binding Affinity of Wild-Type and Recombinant Human Factor IXa Mutant Proteins The relative affinity of the recombinant proteins for heparin was assessed by the position of elution from a heparin-sepharose column in response to a NaCl gradient. Heparin-protein interactions are generally dominated by electrostatic forces, thus, this assay is a reasonable surrogate for direct binding assays. The interaction of the homologous coagulation protease thrombin with heparin has been examined in detail, demonstrating the predominant contribution of electrostatic forces [Olson et al, *J Biol Chem,* 266(10): 6342–52 (1991)]. Likewise, the effect of mutations on the affinity of recombinant thrombins for heparin has previously been assessed by NaCl elution from heparin-sepharose, and correlated with the functional effects of these mutations on inhibition by antithrombin-heparin [Sheehan et al., *Proc Nat'l Acad Sci USA;* 91(12): 5518–22 (1994)].

Substitution of alanine for homologous residues in human factor IXa resulted in an elution of the recombinant factor IXa from the heparin sepharose at a lower concentration of NaCl, consistent with a reduction in heparin affinity.

Plasma-derived factor IX and IXa eluted from heparin-sepharose at 0.49 and 0.58 M NaCl, respectively, suggesting that the activated protease binds with higher affinity than the zymogen form. Wild-type factor IXa eluted similarly to plasma-derived factor IXa, suggesting that any differences in post-translational modifications between these proteins did not affect heparin binding. The remainder of the recombinant factor IXa proteins demonstrated either modest or marked reduction in apparent heparin affinity (elution at lower NaCl concentration). The first group included factor IXa H92A, R170A, and K241A, which demonstrated modest reductions in apparent heparin affinity. The second group included factor IXa IR233A, which demonstrated a marked reduction in apparent heparin affinity (Table D). These data demonstrate that the selected mutations (especially R233A) reduce apparent heparin affinity, suggesting that these residues contribute to a heparin-binding exosite on factor IXa.

The modest effect of single alanine substitutions is not unexpected given the electrostatic, multivalent nature of heparin-protease binding [Olson et al., supra (1991)], and either charge reversal (substitution of glutamate/aspartate) or combinatorial mutants are expected to significantly enhance this effect. The relative effects of these mutations on apparent heparin affinity of factor IXa suggest that the heparin-binding exosite maps to the carboxyl-terminus region of the protease.

EXAMPLE 8

Clotting Activity of Wild-Type and Recombinant Human Factor IXa Mutant Proteins

Clotting activity was examined in a modified activated partial thromboplastin time for both plasma-derived and recombinant factor IXa. Consistent with previous reports, wild-type factor IXa demonstrated approximately 90% of plasma-derived factor IXa clotting activity. This result may be secondary to the presence of a minor factor IX form (4–5%) in which the prosequence has not been cleaved [Bajaj et al., *J Biol Chem,* 272(37): 23418–26 (1997)]. Thus, the wild-type factor IXa clotting activity represents the appropriate control for comparison of the recombinant factor IXa mutant proteins. Factor IXa R233A and K241A demonstrated moderate reductions in clotting activity relative to wild-type, while factor IXa H92A had similar clotting activity to wild-type factor IXa. Likewise, factor IXa R170A was reported to have increased clotting activity relative to wild-type or plasma-derived factor IXa [Chang et al., *J Biol Chem,* 273(20): 12089–94 (1998)]. Thus, the effect of amino acid substitutions on relative heparin affinity can clearly be dissociated from effects on clotting activity.

While the methods and compositions herein have been described in terms of preferred embodiments, it will be apparent that variations may be applied to the methods and/or compositions without departing from the concept, spirit and scope of the invention. More specifically, it will be apparent that assays that are physiologically related may be substituted for the assays described herein while still producing the same or similar results. All such similar substitutes and modifications apparent to those of skill in the art are deemed to be within the scope of the invention as defined by the appended claims.

The present specification cites to certain scientific journal references and patents that, to the extent that they provide exemplary procedural or other information supplemental to that set forth herein, are specifically incorporated herein by reference.

What is claimed is:

1. A mutant human factor IX comprising a mutation in the heparin binding domain which decreases its affinity for heparin as compared to wild-type human factor IX, wherein said mutation is a mutation of the amino acid residue 298, 303, 304, 312, 315, 447, 450, 456, or 458 of SEQ ID NO: 2.

2. The mutant human factor IX of claim 1, wherein said mutation further comprises a substitution of arginine for an alanine at amino acid residue 385 of SEQ ID NO: 2.

3. A mutant human factor IX having a mutation at amino acid residue 450 of SEQ ID NO: 2, wherein said mutation decreases the affinity of said mutant human factor IX for heparin as compared to wild-type human factor IX.

4. The mutant human factor IX of claim 3, wherein said mutation is a substitution of the arginine at amino acid residue 450 of SEQ ID NO: 2 to any other amino acid.

5. The mutant human factor IX of claim 4, wherein arginine at amino acid residue 450 of SEQ ID NO: 2 is substituted with an alanine.

6. A method of treating a subject having hemophilia comprising administering to said subject a composition comprising a mutant human factor IX of claim 1, in an amount effective to promote blood clotting in said subject.

7. The method of claim 6, wherein said mutant human factor IX comprises a mutation of the amino acid located at residue 450 of SEQ ID NO:2.

8. The method of claim 7, wherein the mutant human factor IX comprises a mutation of arginine to an alanine at amino acid residue 450 of SEQ ID NO:2.

9. The method of claim 6, further comprising administering to said subject a composition comprising one or more additional blood clotting factors other than said mutant human factor IX.

10. The method of claim 6, wherein said hemophilia is hemophilia B.

11. A pharmaceutical composition comprising the mutant human factor IX of any one of claims 1 through 5 and a pharmaceutically acceptable carrier, excipient, or diluent.

* * * * *

SEQUENCE LISTING

```
<160> NUMBER OF SEQ ID NOS: 2

<210> SEQ ID NO 1
<211> LENGTH: 1389
<212> TYPE: DNA
<213> ORGANISM: Homo sapiens

<400> SEQUENCE: 1

atgcagcgcg tgaacatgat catggcagaa tcaccaagcc tcatcaccat ctgcctttta     60

ggatatctac tcagtgctga atgtacagtt tttcttgatc atgaaaacgc caacaaaatt    120

ctgaatcggc caaagaggta taattcaggt aaattggaag agtttgttca agggaacctt    180

gagagagaat gtatggaaga aaagtgtagt tttgaagaac cacgagaagt ttttgaaaac    240

actgaaaaga caactgaatt ttggaagcag tatgttgatg gagatcagtg tgagtccaat    300

ccatgtttaa atggcggcag ttgcaaggat gacattaatt cctatgaatg ttggtgtccc    360

tttggatttg aaggaaagaa ctgtgaatta gatgtaacat gtaacattaa gaatggcaga    420

tgcgagcagt tttgtaaaaa tagtgctgat aacaaggtgg tttgctcctg tactgaggga    480

tatcgacttg cagaaaacca gaagtcctgt gaaccagcag tgccatttcc atgtggaaga    540

gtttctgttt cacaaacttc taagctcacc cgtgctgagg ctgtttttcc tgatgtggac    600

tatgtaaatc ctactgaagc tgaaaccatt ttggataaca tcactcaagg cacccaatca    660

tttaatgact tcactcgggt tgttggtgga gaagatgcca aaccaggtca attcccttgg    720

caggttgttt tgaatggtaa agttgatgca ttctgtggag gctctatcgt taatgaaaaa    780

tggattgtaa ctgctgccca ctgtgttgaa actggtgtta aaattacagt tgtcgcaggt    840

gaacataata ttgaggagac agaacataca gagcaaaagc gaaatgtgat tcgagcaatt    900

attcctcacc acaactacaa tgcagctatt aataagtaca accatgacat tgcccttctg    960

gaactggacg aacccttagt gctaaacagc tacgttacac ctatttgcat tgctgacaag   1020

gaatacacga acatcttcct caaatttgga tctggctatg taagtggctg ggcaagagtc   1080

ttccacaaag ggagatcagc tttagttctt cagtacctta gagttccact tgttgaccga   1140

gccacatgtc ttcgatctac aaagttcacc atctataaca acatgttctg tgctggcttc   1200

catgaaggag gtagagattc atgtcaagga gatagtgggg gaccccatgt tactgaagtg   1260

gaagggacca gtttcttaac tggaattatt agctggggtg aagagtgtgc aatgaaaggc   1320

aaatatggaa tatataccaa ggtatcccgg tatgtcaact ggattaagga aaaaacaaag   1380

ctcacttaa                                                           1389

<210> SEQ ID NO 2
<211> LENGTH: 462
```

-continued

<212> TYPE: PRT
<213> ORGANISM: Homo sapiens

<400> SEQUENCE: 2

```
Met Gln Arg Val Asn Met Ile Met Ala Glu Ser Pro Ser Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Pro Arg Glu Val Phe Glu Asn
65                  70                  75                  80

Thr Glu Lys Ile Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Pro Thr Glu Ala Glu
        195                 200                 205

Thr Ile Leu Asp Asn Ile Thr Gln Gly Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ala Ile Ile Pro His His
    290                 295                 300

Asn Tyr Asn Ala Ala Ile Asn Lys Tyr Asn His Asp Ile Ala Leu Leu
305                 310                 315                 320

Glu Leu Asp Glu Pro Leu Val Leu Asn Ser Tyr Val Thr Pro Ile Cys
                325                 330                 335

Ile Ala Asp Lys Glu Tyr Thr Asn Ile Phe Leu Lys Phe Gly Ser Gly
            340                 345                 350

Tyr Val Ser Gly Trp Ala Arg Val Phe His Lys Gly Arg Ser Ala Leu
        355                 360                 365

Val Leu Gln Tyr Leu Arg Val Pro Leu Val Asp Arg Ala Thr Cys Leu
    370                 375                 380

Arg Ser Thr Lys Phe Thr Ile Tyr Asn Asn Met Phe Cys Ala Gly Phe
385                 390                 395                 400
```

-continued

```
His Glu Gly Gly Arg Asp Ser Cys Gln Gly Asp Ser Gly Gly Pro His
                405                 410                 415

Val Thr Glu Val Glu Gly Thr Ser Phe Leu Thr Gly Ile Ile Ser Trp
            420                 425                 430

Gly Glu Glu Cys Ala Met Lys Gly Lys Tyr Gly Ile Tyr Thr Lys Val
        435                 440                 445

Ser Arg Tyr Val Asn Trp Ile Lys Glu Lys Thr Lys Leu Thr
    450                 455                 460
```